United States Patent
Muro Galindo et al.

(10) Patent No.: US 9,655,953 B2
(45) Date of Patent: May 23, 2017

(54) TARGETED PROTEIN REPLACEMENT FOR THE TREATMENT OF LYSOSOMAL STORAGE DISORDERS

(71) Applicants: Icahn School of Medicine at Mount Sinai, New York, NY (US); The Trustees of the University of Pennsylvania, Philadelphia, PA (US)

(72) Inventors: Silvia Muro Galindo, Silver Spring, MD (US); Vladimir R. Muzykantov, Bryn Athyn, PA (US); Edward Howard Schuchman, Haworth, NJ (US)

(73) Assignees: Icahn School of Medicine at Mount Sinai, New York, NY (US); The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 14/516,231

(22) Filed: Oct. 16, 2014

(65) Prior Publication Data
US 2015/0132368 A1 May 14, 2015

Related U.S. Application Data

(63) Continuation of application No. 11/631,248, filed as application No. PCT/US2005/023529 on Jul. 1, 2005, now Pat. No. 8,889,127.

(60) Provisional application No. 60/584,648, filed on Jul. 1, 2004.

(51) Int. Cl.
| | |
|---|---|
| *A61K 9/127* | (2006.01) |
| *A61K 39/00* | (2006.01) |
| *A61K 38/46* | (2006.01) |
| *C12N 9/16* | (2006.01) |
| *C12N 9/14* | (2006.01) |
| *C12P 19/34* | (2006.01) |
| *C12P 21/06* | (2006.01) |
| *C12N 15/00* | (2006.01) |
| *C12N 5/00* | (2006.01) |
| *C07H 21/04* | (2006.01) |
| *A61K 47/48* | (2006.01) |
| *C07K 16/28* | (2006.01) |
| *A61K 38/00* | (2006.01) |

(52) U.S. Cl.
CPC ...... *A61K 38/465* (2013.01); *A61K 47/48561* (2013.01); *C07K 16/2821* (2013.01); *C12N 9/16* (2013.01); *A61K 38/00* (2013.01); *C07K 2317/77* (2013.01); *C07K 2319/035* (2013.01); *C12Y 301/04012* (2013.01); *Y10T 428/2982* (2015.01); *Y10T 428/2991* (2015.01)

(58) Field of Classification Search
CPC .............. A61K 38/00; A61K 47/48561; A61K 38/465; C07K 2319/035; C07K 2317/77; C07K 16/2821; C12N 9/16; Y10T 428/2991; Y10T 428/2982; C12Y 301/04012

USPC .......... 424/450, 178.1, 94.6, 134.1; 435/196, 435/195, 91.1, 69.1, 320.1, 325; 536/23.1, 23.2, 23.4

See application file for complete search history.

(56) References Cited

U.S. PATENT DOCUMENTS

| | | | |
|---|---|---|---|
| 3,966,555 | A | 6/1976 | Arnaud et al. |
| 3,972,777 | A | 8/1976 | Yamada et al. |
| 4,450,238 | A | 5/1984 | Vitobello et al. |
| 4,837,028 | A | 6/1989 | Allen |
| 5,019,369 | A | 5/1991 | Presant et al. |
| 5,382,524 | A | 1/1995 | Desnick et al. |
| 5,401,650 | A | 3/1995 | Desnick et al. |
| 5,433,946 | A | 7/1995 | Allen, Jr. et al. |
| 5,580,757 | A | 12/1996 | Desnick et al. |
| 5,688,766 | A | 11/1997 | Revis |
| 6,066,626 | A | 5/2000 | Yew et al. |
| 6,258,581 | B1 | 7/2001 | Okino et al. |
| 6,350,768 | B1 | 2/2002 | Bohme et al. |
| 6,489,117 | B2 | 12/2002 | Okino et al. |
| 6,537,785 | B1 | 3/2003 | Canfield |
| 6,541,218 | B1 | 4/2003 | Schuchman et al. |
| 6,730,297 | B1 | 5/2004 | Davidson et al. |
| 6,767,741 | B1 | 7/2004 | Epstein et al. |
| RE38,689 | E | 1/2005 | Okino et al. |

(Continued)

FOREIGN PATENT DOCUMENTS

| | | | |
|---|---|---|---|
| JP | 2002/542195 A | | 12/2002 |
| JP | 2003/516122 A | | 5/2003 |

(Continued)

OTHER PUBLICATIONS

Cameron ER., Recent advances in transgenic technology. Molecular Biotechnol., 1997, vol. 7: 253-265.*

(Continued)

*Primary Examiner* — Ganapathirama Raghu
(74) *Attorney, Agent, or Firm* — LeClairRyan, a Professional Corporation

(57) ABSTRACT

The present invention relates to compositions and methods for delivering lysosomal proteins. The compositions and methods described herein permit the targeted delivery of exogenous lysosomal proteins to cell surface proteins that allow their internalization via non-clathrin pathways. The present invention further relates to the use of the compositions and methods for enzyme replacement therapy of lysosomal storage diseases. Nucleic acids, recombinant cells and kits useful for making and using the compositions of the invention are also provided.

5 Claims, 8 Drawing Sheets

(56) References Cited

U.S. PATENT DOCUMENTS

Figures 1A, 1B, 1C:
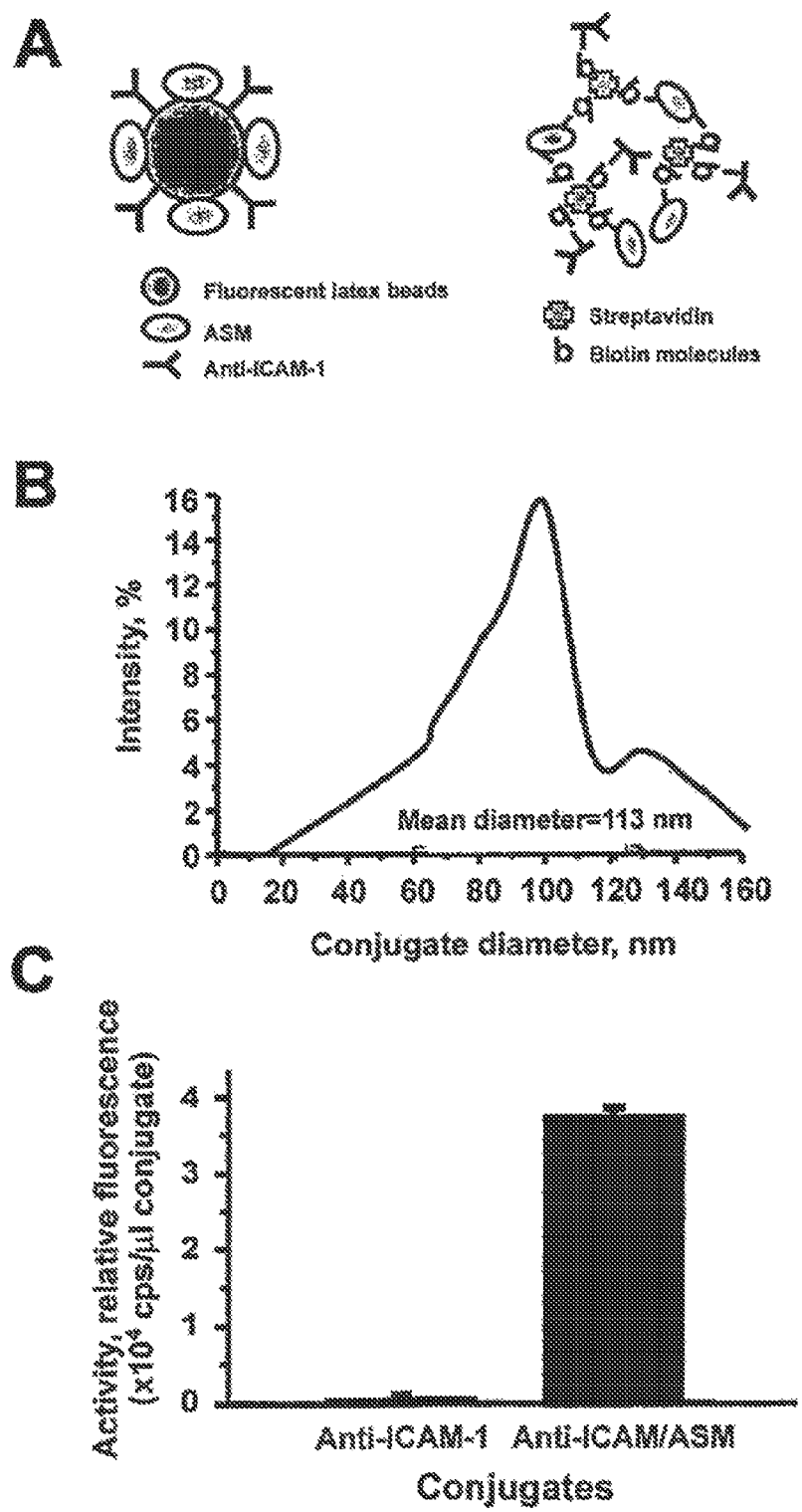

| | | |
|---|---|---|
| 6,858,383 B2 | 2/2005 | Sabbadini |
| 6,881,546 B2 | 4/2005 | Sabbadini |
| 6,884,435 B1 | 4/2005 | O'Hagan et al. |
| 7,018,628 B1 | 3/2006 | Sarkis et al. |
| 7,232,670 B2 | 6/2007 | D'Azzo et al. |
| 7,273,756 B2 | 9/2007 | Adkisson et al. |
| 7,927,587 B2 | 4/2011 | Blazer et al. |
| 8,017,394 B2 | 9/2011 | Adkisson, IV et al. |
| 2003/0087868 A1 | 5/2003 | Yew et al. |
| 2003/0157086 A1 | 8/2003 | Tilly et al. |
| 2003/0211604 A1 | 11/2003 | E. Brown |
| 2003/0215435 A1 | 11/2003 | Berent |
| 2004/0029779 A1 | 2/2004 | Zhu et al. |
| 2004/0039046 A1 | 2/2004 | Deigner |
| 2004/0172665 A1 | 9/2004 | Reuser et al. |
| 2004/0204379 A1 | 10/2004 | Cheng et al. |
| 2004/0242539 A1 | 12/2004 | Fan et al. |
| 2004/0247603 A1 | 12/2004 | Sabbadini |
| 2004/0248262 A1 | 12/2004 | Koeberl et al. |
| 2005/0026823 A1 | 2/2005 | Zankel et al. |
| 2005/0112640 A1 | 5/2005 | Davidson et al. |
| 2006/0154252 A1 | 7/2006 | Marguerie et al. |
| 2007/0009500 A1 | 1/2007 | Blazar et al. |
| 2007/0162992 A1 | 7/2007 | Burns |
| 2007/0184439 A1 | 8/2007 | Guilford et al. |
| 2007/0292949 A1 | 12/2007 | Duguay et al. |
| 2008/0045470 A1 | 2/2008 | Bielawska et al. |
| 2008/0057590 A1 | 3/2008 | Urdea et al. |
| 2008/0199450 A1 | 8/2008 | Schuchman et al. |
| 2008/0248481 A1 | 10/2008 | Rapko et al. |
| 2008/0292618 A1 | 11/2008 | Weisbart |
| 2010/0068302 A1 | 3/2010 | Ramirez De Molina et al. |
| 2010/0160253 A1 | 6/2010 | Coombe et al. |
| 2010/0285139 A1 | 11/2010 | Gulbins |
| 2011/0091439 A1 | 4/2011 | Bernard et al. |
| 2011/0091442 A1 | 4/2011 | Boyd et al. |
| 2014/0287015 A1 | 9/2014 | Schuchman et al. |

FOREIGN PATENT DOCUMENTS

| | | |
|---|---|---|
| JP | 2004/083465 A | 3/2004 |
| WO | WO 90/11353 | 10/1990 |
| WO | WO 00/62780 | 10/2000 |
| WO | WO 01/26678 A1 | 4/2001 |
| WO | WO 02/087510 A2 | 11/2002 |
| WO | WO 2004/057031 A2 | 7/2004 |
| WO | WO 2006/007560 A2 | 1/2006 |
| WO | WO 2006/113289 A2 | 10/2006 |
| WO | WO 2007/089734 A2 | 8/2007 |
| WO | WO 2007/095688 A1 | 8/2007 |
| WO | WO 2007/117096 A2 | 10/2007 |
| WO | WO 2007/136635 A1 | 11/2007 |
| WO | WO 2008/086296 A2 | 7/2008 |
| WO | 2008148063 A1 | 12/2008 |
| WO | 2009155936 A1 | 12/2009 |
| WO | WO 2010/127355 A1 | 11/2010 |
| WO | WO 2011/025996 A2 | 3/2011 |
| WO | 2011066352 A1 | 6/2011 |
| WO | WO 2012/051415 A2 | 4/2012 |
| WO | WO 2012/154794 A2 | 11/2012 |
| WO | WO 2012/177778 A1 | 12/2012 |
| WO | WO 2013/036875 A1 | 3/2013 |
| WO | WO 2013/101276 A2 | 7/2013 |
| WO | WO 2013/181530 A1 | 12/2013 |
| WO | WO 2014/160390 A1 | 10/2014 |

OTHER PUBLICATIONS

Couzin et al., As Gelsinger case ends, Gene therapy suffers another blow. Science, 2005, vol. 307: 1028.*
Donsante et al., AAV vector integration sites in mouse hepatocellular carcinoma. Science, 2007. vol. 317: 477.*
Juengst ET., What next for human gene therapy? BMJ., 2003, vol. 326:1410-1411.*
Kappel et al., Regulating gene expression in transgenic animals. Current Opinion in Biotechnology 1992, vol. 3: 548-553.*
Kimmelman J., Recent developments in gene transfer: risk and ethics. BMJ, 2005, vol. 350; 79-82.*
Mullins et al., Transgenesis in nonmurine species. Hypertension, 1993, vol. 22 (4): 630-633.*
Mullins et al., Transgenesis in the rat and larger mammals. J. Clin. Invest., 1996, vol. 97 (7): 1557-1560.*
Raper SE., Gene therapy: The good, the bad, and the ugly. Surgery, 2005, vol. 137(5): 487-492.*
Rosenberg et al., Gene therapist, heal thyself. Science, 2000, vol. 287: 1751.*
Touchette et al., Gene therapy: Not ready for prime time. Nat. Med., 1996, vol. 2(1 ): 7-8.*
Wigley et al., Site-specific transgene insertion: an approach. Reprod. Fert. Dev., 1994, vol. 6: 585-588.*
Wolf JA., The "grand" problem of synthetic delivery. Nat. Biotechnol., 2002, vol. 20: 768-769.*
Achord et al., 1978, "Human beta-glucuronidase: in vivo clearance and in vitro uptake by a glycoprotein recognition system on reticuloendothelial cells." in Cell; 15(1):269-78.
Almenar-Queralt et al., 1995, "Apical topography and modulation of ICAM-1 expression on activated endothelium." in Am. J. Pathol.; 147(5):1278-88.
Barton et al., 1990, "Therapeutic response to intravenous infusions of glucocerebrosidase in a patient with Gaucher disease." in Proc. Natl. Acad. Sci. USA; 87(5): 1913-6.
Berlin and Oliver, 1980, "Surface functions during mitosis", J Cell Biol, 85:660-671.
Bernstein et al., 1989, "Fabry disease: six gene rearrangements and an exonic point mutation in the alpha-galactosidase gene." in J. Clin. Invest.; 83(4):1390-1399.
Beutler et al., 1972, "Purification and Properties of human alpha-galactosidases." in J. Biol. Chem.; 247(22):7195-7200.
Bhowmick et al., 2012, "Effect of flow on endothelial endocytosis of nanocarriers targeted to ICAM-1", J Controlled Release, 157(3):485-492.
Bishop et al., 1980, "Purification and characterization of human alpha-galactosidase isozymes: comparison of tissue and plasma forms and evaluation of purification methods." in Birth Defects Original Article Series; XVI(1):17-32.
Bishop et al., 1981, "Affinity purification of alpha-galactosidase A from human spleen, placenta, and plasma with elimination of pyrogen contamination. Properties of the purified splenic enzyme compared to other forms." in J. Biol. Chem.; 256(3):1307-1316.
Bishop et al., 1981, "Enzyme Therapy XX: Further Evidence for the Differential In Vivo Fate of Human Splenic and Plasma . . . ", in Lysosomes and Lysosomal Storage Diseases, Eds. Callahan et al. Raven Press; 381-94.
Bishop et al., 1985, "Molecular Cloning and Nucleotide Sequencing of a Complementary DNA Encoding Human Alpha Galactosidase A" in Am. J. Hum. Genetics 37 (4 Suppl):A144.
Bishop et al., 1986, "Human alpha-galactosidase A: nucleotide sequence of a cDNA clone encoding the mature enzyme." in Proc. Natl. Acad. Sci.; 83(13):4859-4863.
Bishop et al., 1988, "Human α-galactosidase:characterization and eukaryotic expression of the full-length cDNA and structural organization of the gene" in Lipid Storage Disorders, Eds. Salvayre et al. Plenum Publishing Corp 809-822.
Bishop et al., 1988, "Structural organization of the human alpha-galactosidase A gene: further evidence for the absence of a 3' untranslated region." in Proc. Natl. Acad. Sci.; 85(11):3903-3907.
Bonten et al., 2004, "Targeting macrophages with baculovirus-produced lysosomal enzymes: implications for enzyme replacement therapy of the glycoprotein storage disorder galactosialidosis." in FASEB J; 18(9):971-3.
Boose et al., 1991, "Conditional intercellular cohesion in a Dictyostelium discoideum mutant which is temperature sensitive for correct processing of asparagine-linked oligosaccharides." in Glycobiology; 1(3):295-305.
Brady et al., 1973, "Replacement therapy for inherited enzyme deficiency. Use of purified ceramidetrihexosidase in Fabry's disease." in N. Engl. J. Med.; 289(1):9-14.

(56) References Cited

OTHER PUBLICATIONS

Brady et al., 1994, "Modifying exogenous glucocerebrosidase for effective replacement therapy in Gaucher disease." J. Inherit. Dis.; 17(4):510-9.
Brady et al., 2003, "Enzyme replacement therapy: conception, chaos and culmination." in Phil. Trans. R. Soc. London B Biol. Sci.; 358(1433):915-9.
Cabrera-Salazar et al., 2002, "Gene therapy for the lysosomal storage disorders." in Curr. Opin. Mol. Ther.; 4(4):349-58.
Calhoun et al., 1985, "Fabry disease: isolation of a cDNA clone encoding human alpha-galactosidase A." in Proc. Natl. Acad. Sci.; 82(21):7364-7368.
Callahan et al., 1973, "Alpha-N-acetylgalactosaminidase: isolation, properties and distribution of the human enzyme." in Biochemical Med.; 7(3):424-431.
Chelikani et al., 2004, "Diversity of structures and properties among catalases", Cell Mol Life Sci, 61(192-208).
Christofidou-Solomidou et al., 2002, "Vascular immunotargeting of glucose oxidase to the endothelial antigens induces distinct forms of oxidant acute lung injury: targeting to thrombomodulin, but not to PECAM-1, causes pulmonary thrombosis and neutrophil transmigration." in Am. J. Pathol.; 160(3):1155-69.
Coppola et al., 1989, "Construction of . Baculovirus Derivatives that overproduce Human α-galactosidase A" in J. Cell. Biochem. Suppl. Abstract No. K306; 13D:227-347.
Conner and Schmid, 2003, "Regulated portals of entry into the cell", Nature, 422:37-44.
D'Azzo, 2003, "Gene transfer strategies for correction of lysosomal storage disorders." in Acta Haematol.; 110(2-3):71-85.
Dean et al., 1977, "The identification of alpha-galactosidase B from human liver as an alpha-N-acetylgalactosaminidase." in Biochem. Biophys. Res. Commun.; 77(4):1411-1417.
Dean et al.., 1979, "Studies on human liver alpha-galactosidases. II. Purification and enzymatic properties of alpha-galactosidase B (alpha-N-acetylgalactosaminidase)." in J. Biol. Chem.; 254(20):10001-10005.
Desnick et al., 1979, "Enzyme therapy in Fabry disease: differential in vivo plasma clearance and metabolic effectiveness of plasma and splenic alpha-galactosidase A isozymes." in Proc. Nalt. Acad. Sci. USA; 76(10):5326-5330.
Desnick et al., 1980, "Enzyme therapy XVII: metabolic and immunologic evaluation of alpha-galactosidase A replacement in Fabry disease." in Birth Defects Original Article Series; XVI(1):393-413.
Desnick et al., 1987, "Fabry disease: molecular diagnosis of hemizygotes and heterozygotes." in Enzyme; 38(1-4):54-64.
Desnick et al., 1989, "Fabry Disease: α-Galactosidase Deficiency; Schindler Disease: αN-Acetylgalactosaminidase Deficiency." in The Metabolic Basis of Inherited Disease, eds. Scriver et al. McGraw Hill, NY; 70:1751-96.
Desnick et al., 1990, "Schindler disease: an inherited neuroaxonal dystrophy due to alpha-N-acetylgalactosaminidase deficiency." in J. Inher. Metab. Dis.; 13:549-559.
Desnick et al., 2002, "Enzyme replacement and enhancement therapies: lessons from lysosomal disorders." in Nature Rev. Genet.; 3(12):954-66.
Dhami et al., 2004, Mannose 6-phosphate receptor-mediated uptake is defective in acid sphingomyelinase-deficient macrophages: implications for Niemann-Pick disease enzyme replacement therapy. J. Biol. Chem.; 279(2):1526-32.
Diamond et al., 1991, "Binding of the integrin Mac-1 (CD11b/CD18) to the third immunoglobulin-like domain of ICAM-1 (CD54) and its regulation by glycosylation" in Cell; 65:961-71.
Ellinwood et al., 2004, "Gene therapy for lysosomal storage diseases: the lessons and promise of animal models." in J. Gene Med.; 6(5):481-506.
Estruch et al., 2001, "Non-viral, integrin-mediated gene transfer into fibroblasts from patients with lysosomal storage diseases." in J. Gene Med.; 3(5):488-97.
Fawcett, 1965, "Surface specializations of absorbing cells", J Histochem Cytochem, 13(2):75-91.

Ferlinz et al., 1994, "Occurrence of two molecular forms of human acid shingomyelinase", Biochem J, 301:855-862.
Ferlinz et al., 1997, "Functional characterization of the N-glycosylation sites of human acid sphingomyelinase by site-directed mutagenesis", Eur J Biochem; 243:511-517.
Friedman et al., 1999, "A comparison of the pharmacological properties of carbohydrate remodeled recombinant and placental-derived beta-glucocerebrosidase: implications for clinical efficacy in treatment of Gaucher disease." Blood; 93(9):2807-16.
Furbish et al., 1981, "Uptake and distribution of placental glucocerebrosidase in rat hepatic cells and effects of sequential deglycosylation." in Biochem. Biophys. Acta; 673(4):425-34.
Garman et al., 2002, "The 1.9 Å Structure of α-N-Acetylgalactosaminidase", Structure; 10(3):425-434.
Garman & Garboczi, 2004, "The molecular defect leading to fabry disease: structure of human α-galactosidase", J Mol Biol; 337(2):319-335.
Gole et al., 2000, "Plasma proteins modified by tyrosine nitration in acute respiratory distress syndrome." in Am. J. Physiol. Lung Cell Mol. Physiol.; 278(5):L961-967.
Grabowski et al., 2003, "Enzyme therapy for lysosomal storage disease: principles, practice, and prospects." in Annu. Rev. Genomics Hum. Genet.; 4:403-36.
Hanzopoulos & Calhoun, 1987, "Expression of the human alpha-galactosidase A in *Escherichia coli* K-12." in Gene (Amst.); 57(2-3):159-169.
Hasholt & Sorenson, 1986, "Lysosomal alpha-galactosidase in endothelial cell cultures established from a Fabry hemizygous and normal umbilical veins." in Human Genet. 72(1):72-76.
Haskins et al., 1996, "Bone marrow transplantation therapy for metabolic disease: animal models as predictors of success and in utero approaches." in Bone Marrow Transplant; 18(Suppl. 3): S25-S27.
He et al., 1999, "Characterization of human acid sphingomyelinase purified from the media of overexpressing Chinese hamster ovary cells." in Biochim. Biophys. Acta; 1432(2):251-64.
Hers et al., Jan. 1963, "alpha-Glucosidase deficiency in generalized glycogenstorage disease (Pompe's disease)." in Biochem J., 86:11-16.
Hlavacek et al., 1999, "Steric effects on multivalent ligand-receptor binding: exclusion of ligand sites by bound cell surface receptors", Biophysical J, 76:3031-3043.
Hoogerbrugge et al., Jun. 1998, "Effect of bone marrow transplantation on enzyme levels and clinical course in the neurologically affected twitcher mouse." in J. Clin. Invest.; 81(6): 1790-4.
Ioannou et al., 1990, "Cloning and Expression of Biologically Active α-Galactosidase A as a Fusion Protein" in Inborn Errors of Metabolism. 5th International Congress, Abstract No. OC4.3.
Jin et al., 2002, "Intracerebral transplantation of mesenchymal stem cells into acid sphingomyelinase-deficient mice delays the onset of neurological abnormalities and extends their life span." in J. Clin. Invest.; 109(9):1183-91.
Jin et al., 2003, "Ex vivo gene therapy using bone marrow-derived cells: combined effects of intracerebral and intravenous transplantation in a mouse model of Niemann-Pick disease." in Mol. Ther.; 8(6):876-85.
Kaplan et al., 1977, "Phosphohexosyl components of a lysosomal enzyme are recognized by pinocytosis receptors on human fibroblasts." in Proc. Natl. Acad. Sci. USA; 74(5):2026-30.
Klabunde et al., 1996, "Mechanism of Fe(III)-Zn(II) purple acid phosphatase based on crystal structures", J Mol Biol; 259:737-748.
Kölzer et al., 2004, "Functional characterization of the postulated intramolecular sphingolipid activator protein domain of human acid sphingomyelinase", Biol Chem; 385:1193-1195.
Kornfeld et al., 1982, "Steps in the phosphorylation of the high mannose oligosaccharides of lysosomal enzymes." in CIBA Found. Symp.; (92):138-56.
Kornfeld et al., 1987, "Trafficking of lysosomal enzymes." in FASEB J.; 1(6):462-468.
Kornfeld et al., 1990, "Lysosomal enzyme targeting." in Biochem. Soc. Trans. 18(3):367-74.
Kornreich et al., 1989, "Nucleotide sequence of the human alpha-galactosidase A gene." in Nuc. Acids. Res.; 17(8):3301-3302.

(56) References Cited

OTHER PUBLICATIONS

Kornreich et al., 1990, "Alpha-galactosidase A gene rearrangements causing Fabry disease. Identification of short direct repeats at breakpoints in an Alu-rich gene." in J. Biol. Chem.; 265(16): 9319-9326.

Kozower et al., 2003, "Immunotargeting of catalase to the pulmonary endothelium alleviates oxidative stress and reduces acute lung transplantation injury." in Nat Biotechnol; 21(4):392-8.

Krivit et al., 1992, "State of the art review. Bone marrow transplantation treatment for storage diseases. Keystone." in Bone Marrow Transplant.; 10(Suppl. 1): 87-96.

Kusiak et al., 1978, "Purification and properties of the two major isozymes of alpha-galactosidase from human placenta." in J. Biol. Chem.; 253(1):184-190.

Lansmann et al., 2003, "Human acid sphingomyelinase—Assignment of the disulfide bond pattern", Eur. J. Biochem. 270: 1076-1088.

Lebowitz et al., 2004, "Glycosylation-independent targeting enhances enzyme delivery to lysosomes and decreases storage in mucopolysaccharidosis type VII mice." in Proc. Natl. Acad. Sci. USA; 101(9):3083-8.

Leimig et al., 2002, "Functional amelioration of murine galactosialidosis by genetically modified bone marrow hematopoietic progenitor cells." in Blood; 99(9): 3169-78.

Lemansky et al., 1987, "Synthesis and processing of alpha-galactosidase A in human fibroblasts. Evidence for different mutations in Fabry disease." in J. Biol. Chem.; 262(5):2062-2065.

Lin et al., 1998, "Caenorhabditis elegans contains two distinct acid sphingomyelinases", J Biol Chem; 273(23):14374-14379.

Malatack et al., 2003, "The status of hematopoietic stem cell transplantation in lysosomal storage disease." in Pediatr. Neurol.; 29(5):391-403.

Meikle et al., 1999, "Prevalence of lysosomal storage disorders." in JAMA; 281(3): 249-54.

Mintzer et al., 2005, "A novel high-throughput screening format to identify inhibitors of secreted acid sphingomyelinase." in J Biomol Screen; 10(3):225-34.

Miranda et al., 1997, "Bone marrow transplantation in acid sphingomyelinase-deficient mice: engraftment and cell migration into the brain as a function of radiation, age, and phenotype." in Blood; 90(1):444-52.

Miranda et al., 1998, "Biochemical, pathological, and clinical response to transplantation of normal bone marrow cells into acid sphingomyelinase-deficient mice." in Transplantation; 65(7):884-92.

Miranda et al., 2000, "Hematopoietic stem cell gene therapy leads to marked visceral organ improvements and a delayed onset of neurological abnormalities in the acid sphingomyelinase deficient mouse model of Niemann-Pick disease." in Gene Ther.; 7(20):1768-76.

Miranda et al., 2000, "Infusion of recombinant human acid sphingomyelinase into niemann-pick disease mice leads to visceral, but not neurological, correction of the pathophysiology." in FASEB J.; 14(13):1988-95.

Mistry et al., 1996, "Therapeutic delivery of proteins to macrophages: implications for treatment of Gaucher's disease." Lancet; 348(9041):1555-9.

Murciano et al., 2003, "ICAM-directed vascular immunotargeting of antithrombotic agents to the endothelial luminal surface." in Blood; 101(10):3977-84.

Muro et al., 2003, "A novel endocytic pathway induced by clustering endothelial ICAM-1 or PECAM-1." in J Cell Sci; 116(Pt 8):1599-609.

Muro et al., 2003, "Slow intracellular trafficking of catalase nanoparticles targeted to ICAM-1 protects endothelial cells from oxidative stress." in Am J Physiol Cell Physiol; 285(5):C1339-47.

Muro et al., 2004, "Endothelial endocytic pathways: gates for vascular drug delivery." in Curr Vasc Pharmacol; 2(3):281-99.

Muro et al., 2005, "ICAM-1 recycling in endothelial cells: a novel pathway for sustained intracellular delivery and prolonged effects of drugs." in Blood; 105(2):650-8.

Murray, 1987, "Lectin-specific targeting of lysosomal enzymes to reticuloendothelial cells." in Meth. Enzymol.; 149:25-42.

Newman et al., 1997, "The biology of PECAM-1." in J. Clin. Invest.; 99(1):3-8.

Newrzella et al., 1992, "Molecular cloning of the acid sphingomyelinase of the mouse and the organization and complete nucleotide sequence of the gene", Biol Chem Hoppe-Seyler; 373:1233-1238.

Newrzella et al., 1996, "Functional analysis of the glycosylation of murine acid sphingomyelinase", J Biol Chem; 271(50):32089-32095.

Pittis et al., 2004, "Acid sphingomyelinase: identification of nine novel mutations among Italian Niemann Pick Type B patients and characterization of in vivo functional in-frame start codon", Human Mutation, Mutation in Brief #734 p. 1-7.

Ponting, 1994, "Acid phingomyelinase possesses a domain homologous to its activator proteins: saposins B and D", Protein Science; 3:359-361.

Pratico et al., 1997, "Localization of distinct F2-isoprostanes in human atherosclerotic lesions." in J. Clin. Invest.; 100(8):2028-34.

Prince et al., 2004, "Lipoprotein receptor binding, cellular uptake, and lysosomal delivery of fusions between the receptor-associated protein (RAP) and alpha-L-iduronidase or acid alpha-glucosidase." in J Biol. Chem.; 279(33):35037-46.

Qui et al., 2003, "Activation of human acid sphingomyelinase through modification or deletion of c-terminal cysteine", J Biol Chem; 278(35):32744-32752.

Quinn et al, 1987, "A genomic clone containing the promoter for the gene encoding the human lysosomal enzyme, alpha-galactosidase A." in Gene (Amst.); 58(2-3): 177-188.

Quintern et al., 1987, "Acid sphingomyelinase from human urine: purification and characterization", Biochimica et Biophysica Acta; 922:323-336.

Rousseau et al., 1986, "Utilization of membranous lipid substrates by membranous enzymes: activation of the latent sphingomyelinase of hen erythrocyte membrane." in Arch. Biochem. Biophys.; 244(2):838-45.

Sands et al., 2001, "Biodistribution, kinetics, and efficacy of highly phosphorylated and non-phosphorylated beta-glucuronidase in the murine model of mucopolysaccharidosis VII." in J. Biol. Chem.; 276(46):43160-5.

Schindler et al., 1989, "Neuroaxonal dystrophy due to lysosomal alpha-N-acetylgalactosaminidase deficiency." in New Eng. J. Med.; 320(26):1735-1740.

Schram et al., 1977, "The identity of alpha-galactosidase B from human liver." in Biochimica et Biophysica Acta; 482(1):138-144.

Schuchman et al., 1991, "Human acid sphingomyelinase. Isolation, nucleotide sequence and expression of the full-length and alternatively spliced cDNAs.", J Biol Chem.; 266(13):8531-8539.

Scriver et al., 2000, Part 16: Lysosomal Disorders in: The Metabolic and Molecular Bases of Inherited Disease, $8^{th}$ ed., McGraw-Hill.

Springer et al., 1994, "Traffic signals for lymphocyte recirculation and leukocyte emigration: the multistep paradigm." in Cell; 76(2):301-14.

Stahl et al., 1978, "Evidence for receptor-mediated binding of glycoproteins, glycoconjugates, and lysosomal glycosidases by alveolar macrophages." in Proc. Natl. Acad. Sci. USA; 75(3):1399-403.

Sweeley et al., 1983, "Post-translational processing reactions involved in the biosynthesis of lysosomal alpha-N-acetylgalactosaminidase in cultured human fibroblasts." in Archives of Biochem & Biophys.; 233(1):158-65.

Tang et al., 1993, "Identification of PECAM-1 in solid tumor cells and its potential involvement in tumor cell adhesion to endothelium", J Biol Chem; 268(30):22883-22894.

Taylor et al., 1997, "Decreased lysosomal storage in the adult MPS VII mouse brain in the vicinity of grafts of retroviral vector-corrected fibroblasts secreting high levels of beta-glucuronidase." in Nature Med.; 3(7): 771-74.

(56) References Cited

OTHER PUBLICATIONS

Tsuji et al., 1987, "Signal sequence and DNA-mediated expression of human lysosomal alpha-galactosidase A." in Eur. J. Biochem; 165(2):275-280.
Tsuji et al., 1989, "Molecular cloning of a full-length cDNA for human alpha-N-acetylgalactosaminidase (alpha-galactosidase B)." in Biochem. Biophys. Res. Commun.; 163(3):1498-1504.
Vanier et al., 2013, "Niemann-Pick diseases", Handbook of Clinical Neurology, 113(3rd series):1717-1721.
Vellodi et al., 1997, "Bone marrow transplantation for mucopolysaccharidosis type I: experience of two British centres." in Arch. Dis. Child.; 76(2):92-99.
Voraberger et al., 1991, "Cloning of the human gene for intercellular adhesion molecule 1 and analysis of its 5'-regulatory region", J Immunol; 147(8):2777-2786.
Waheed et al., 1988, "Human lysosomal acid phosphatase is transported as a transmembrane protein to lysosomes in transfected baby hamster kidney cells." in EMBO J.; 7(8):2351-8.
Wang et al., 1988, "Schindler Disease Biochemical and Molecular Characterization of a New Neuroaxonal Dystrophy Due to Alpha-N Acetylgalactosaminidase Deficiency" in Am. J. Hum. Genet; 43 (3 Suppl):A99.
Wang et al., 1989, "Molecular Genetics of PKU in Orientals" in Am J. Hum. Genet; 45 (4 Suppl) A228.
Wang et al., 1990, "Human alpha-N-acetylgalactosaminidase-molecular cloning, nucleotide sequence, and expression of a full-length cDNA. Homology with human alpha-galactosidase A suggests evolution from a common ancestral gene." in J. Biol. Chem.; 265(35): 21859-21866.
Wang et al., 1990, "Schindler disease: the molecular lesion in the alpha-N-acetylgalactosaminidase gene that causes an infantile neuroaxonal dystrophy." in J. Clin. Invest; 86(5):1752-1756.
Weinstein et al., 1987, "Primary structure of beta-galactoside alpha 2,6-sialyltransferase. Conversion of membrane-bound enzyme to soluble forms by cleavage of the NH2-terminal signal anchor." in J. Biol. Chem; 262(36):17735-43.
Wiewrodt et al., 2002, "Size-dependent intracellular immunotargeting of therapeutic cargoes into endothelial cells." in Blood; 99(3):912-22.
Yamauchi et al., 1990, "Molecular cloning of two species of cDNAs for human alpha-N-acetylgalactosaminidase and expression in mammalian cells." in Biochem. Biophys. Res. Commun.; 170(1):231-37.
Yeyati et al., 1995, "Fluorescence-based selection of retrovirally transduced cells in the absence of a marker gene: direct selection of transduced type B Niemann-Pick disease cells and evidence for bystander correction." in Hum. Gene Ther.; 6(8):975-83.
Zhang et al., 2005, "Delivery of beta-galactosidase to mouse brain via the blood-brain barrier transferrin receptor." in J. Pharmacol. Exp. Ther.; 313(3):1075-81.
Zhu et al., 2004, "Dexamethasone-mediated up-regulation of the mannose receptor improves the delivery of recombinant glucocerebrosidase to Gaucher macrophages." in J. Pharmacol. Exp. Ther.; 308(2):705-11.
Agnieszka et al., "Prenatal Diagnosis—Principles of Diagnostic Procedures and Genetic Counseling," *Folia Histochemica et Cytobiologica* 45:11-16 (2007).
Auclair et al., "Intra-Articular Enzyme Administration for Joint Disease in Feline Mucopolysaccharidosis VI: Enzyme Dose and Interval," *Pediatr. Res.* 59(4):538-43 (2006).
Bawab et al., "Ceramidases in the Regulation of Ceramide Levels and Function," *Subcellular Biochemistry*, vol. 36, Chapter 10, Phospholipid Metabolism in Apoptosis, Quinn et al., Eds., Kluwer Academic/Plenum Publishers, New York (2002).
Bazian, "Ultra Drug Orphan Drugs for Lysosomal Storage Disorders: A Guideline Comparison and Survey of International Current Practice," 1-70 (2009).
Becker et al., "Acid Sphingomyelinase Inhibitors Normalize Pulmonary Ceramide and Inflammation in Cystic Fibrosis," *Am. J. Respir. Cell Mol. Biol.* 42:716-24 (2010).

Bernardo et al., "Purification, Characterization, and Biosynthesis of Human Acid Ceramidase," *J. Biol. Chem.* 270(19):11098-11102 (1995).
Beutler, E., "Gaucher Disease: New Molecular Approaches to Diagnosis and Treatment," *Science* 256:794-799 (1992).
Bielicki et al., "Advantages of Using Same Species Enzyme for Replacement Therapy in a Feline Model of Mucopolysaccharidosis Type VI," *The Journal of Biological Chemistry* 274(51):36335-36343 (1999).
Bielicki et al., "Recombinant Canine alpha-L-Fucosidase: Expression, Purification, and Characterization," *Mol. Gen. Metabolism* 69:24-32 (2000).
Bodas et al., "Critical Modifier Role of Membrane-Cystic Fibrosis Transmembrane Conductance Regulator-Dependent Ceramide Signaling in Lung Injury and Emphysema," *J. Immunol.* 186:602-613 (2011).
Broun et al., "Catalytic Plasticity of Fatty Acid Modification Enzymes Underlying Chemical Diversity of Plant Lipids," *Science* 282:1315-1317 (1998).
Chavez et al., "Acid Ceramidase Overexpression Prevents the Inhibitory Effects of Saturated Fatty Acids in Insulin Signaling," *J. Biol. Chem.* 280(20):20148-53 (2006).
Chica et al., "Semi-Rational Approaches to Engineering Enzyme Activity: Combining the Benefits of Directed Evolution and Rational Design," *Curr. Opi. Biotechnol.* 16:378-384 (2005).
Daly & Sands, "Gene Therapy for Lysosomal Storage Diseases," *Expert Opin. Invest. Drugs* 7(10):1673-82 (1998).
Devos et al., "Practical Limits of Function Prediction," *Proteins: Structure, Function, and Genetics* 41:98-107 (2000).
Eliyahu et al., "Acid Ceramidase Improves the Quality of Oocytes and Embryos and the Outcome of in Vitro Fertilization," *FASEB J.* 24:1229-38 (2010).
Eliyahu et al., "Acid Ceramidase is a Novel Factor Required for Early Embryo Survival," Abstract Presented in Mar. 2007.
Eliyahu et al., "Acid Ceramidase is a Novel Factor Required for Early Embryo Survival," *FASEB J.* 21:1403-09 (May 2007).
Eliyahu et al., "Anti-TNF-Alpha Therapy Enhances the Effects of Enzyme Replacement Therapy in Rats with Mucopolysaccharidosis Type VI," *PLOS One* 6(8):e22447 (2011).
Eliyahu et al., "Identification of Cystatin SA as a Novel Inhibitor of Acid Ceramidase," *J. Biol. Chem.* 286(41):35624-33 (2011).
Eng et al., "Safety and Efficacy of Recombinant Human alpha-Galactosidase A Replacement Therapy in Fabry's Disease," N. Eng. J. Med. 345(1):9-16 (2001).
European Patent Application No. 08727393.4, Supplementary European Search Report (Sep. 9, 2010).
European Patent Office Communication and Examination Report for European Patent Application No. 08727393.4 (Dec. 4, 2014).
Extended European Search Report and Opinion for European Patent Application No. 12830086.0 (dated Jul. 13, 2015).
Extended European Search Report for European Patent Application No. 12803458.4 (dated Mar. 20, 2015).
Farkas et al., "The Recycling of Apolipoprotein E and its Amino-Terminal 22 kDa Fragment: Evidence of Multiple Redundant Pathways," *J. Lipid Res.* 45:1546-1554 (2004).
First Office Action and English Translation for Chinese Patent Application No. 201280037341.5 (mailed Dec. 3, 2014).
Fox et al., "Circulating Sphingolipid Biomarkers in Models of Type 1 Diabetes," *Journal of Lipid Research*, 30 pp., retrieved from www.jlr.org on Jan. 6, 2011.
Gao et al., "Delivery of a Retroviral Vector Expressing Human beta-Glucuronidase to the Liver and Spleen Decreases Lysosomal Storage in Mucopolysaccharidosis VII Mice," *Mol. Ther.* 2(2):233-44 (2000).
Gilbert et al., "Sphingomyelinase Decreases Type II Collagen Expression in Bovine Articular Cartilage Chondrocytes via the ERK Signaling Pathway," *Arthritis & Rheumatism* 58(1):209-220 (2008).
Grabowski et al., "Enzyme Therapy in Type 1 Gaucher Disease: Comparative Efficacy of Mannose-Terminated Glucocerebrosidase from Natural and Recombinant Sources," *Ann. Intern. Med.* 122:33-39 (1995).

(56) References Cited

OTHER PUBLICATIONS

Grassme et al., "CTFR-Dependent Susceptibility of the Cystic Fibrosis-Host to Pseudomonas aeruginosa," *Int. J. Med. Microbiol.* 300:578-583 (2010).
Harmatz et al., "Enzyme Replacement Therapy in Mucopolysaccharidosis VI (Maroteaux-Lamy Syndrome)," *J. Pediatr.* 144:574-80 (2004).
He et al., "Deregulation of Sphingolipid Metabolism in Alzheimer's Disease," *Neurobiology of Aging* 31(3):398-408 (2010).
He et al., "Purification and Characterization of Recombinant, Human Acid Ceramidase. Catalytic Reactions and Interactions With Acid Sphingomyelinase," *J. Biol. Chem.* 278(35):32978-86 (2003).
Huang et al., "A Comparison of the Signal Pathways Between the TNFalpha- and Oridonin-Induced Murine L929 Fibrosarcoma Cell Death," *Acta Med. Okayama* 59(6):261-70 (2005).
Huang et al., "Elevation of the Level and Activity of Acid Ceramidase in Alzheimer's Disease Brain," *Europ. J. Neurosci.* 20:3489-3497 (2004).
International Preliminary Report on Patentability for PCT/US2008/050418 (mailed Jul. 16, 2009).
International Search Report and Written Opinion for PCT/US2008/050418 (mailed Oct. 8, 2008).
International Search Report and Written Opinion for International Application No. PCT/US05/23529 (mailed Aug. 2, 2006).
International Search Report and Written Opinion for International Application No. PCT/US2014/026481 (mailed Aug. 11, 2014).
International Search Report and Written Opinion for PCT Application No. PCT/US2012/043369 (mailed Aug. 31, 2012).
International Search Report and Written Opinion for PCT/US10/33422 (mailed Jun. 29, 2010).
International Search Report and Written Opinion for PCT/US11/56147 (mailed Apr. 26, 2012).
International Search Report and Written Opinion for PCT/US13/043608 (mailed Oct. 21, 2013).
International Search Report and Written Opinion for PCT/US2012/031847 (dated Jul. 22, 2013).
Internatonal Search Report and Written Opinion for PCT/US2012/054316 (mailed Dec. 20, 2012).
Ioannou et al., "Fabry Disease: Preclinical Studies Demonstrate the Effectiveness of alpha-Galactosidase A Replacement in Enzyme-Deficient Mice," *Am J. Hum. Genet.* 68:14-25 (2001).
Isemura et al., "Characterization and Amino Acid Sequence of New Acidic Cysteine Proteinase Inhibitor (Cystatin SA) Structurally Closely Related to Cystatin S, From Human Whole Saliva," *J. Biochem.* 102(4):693-704 (1987).
Jan et al., "Sindbis Virus Entry Into Cells Triggers Apoptosis by Activating Sphingomyelinase,"*J. Virol.* 74(14):6425-32 (2000).
Kakkis et al., "Long-Term and High-Dose Trials of Enzyme Replacement Therapy in the Canine Model of Mucopolysaccharidosis I," *Biochem. Mol. Med.* 58:156-67 (1996).
Kato et al., "Cystatin SA, A Cysteine Proteinase Inhibitor, Induces Interferon-Gamma Expression in CD4-Positive T Cells," *Biol. Chem.* 385(5):419-22 (2004).
Kishida et al., "Docosahexaenoic Acid Enrichment Can Reduce L929 Cell Necrosis Induced by Tumor Necrosis Factor," *Biochim. Biophys. Acta* 1761:454-62 (2006).
Kisselev, L., "Polypeptide Release Factors in Prokaryotes and Eurkaryotes: Same Function, Different Structure," *Structure* 10:8-9 (2002).
Le Roy et al., "Clathrin-and non-Clathrin Mediated Endocytic Regulation of Cell Signalling," *Nature* 6:112-126 (2005).
Li et al., "Insertional Mutagenesis of the Mouse Acid Ceramidase Gene Leads to Early Embryonic Lethality in Homozygotes and Progressive Lipid Storage Disease in Heterozygotes," *Genomics* 79(2):218-24 (2002).
Liu et al., "Acid Ceramidase Upregulation in Prostate Cancer: Role in Tumor Development and Implications for Therapy," *Expert Opinions in Therapeutic Targets* 13(12):1449-1458 (2009).

Macrae et al., "Ceramide Inhibition of Chondrocyte Proliferation and Bone Growth is IGF-I Independent," *Journal of Endocrinology* 191:369-377 (2006).
Mao et al., "Cloning and Characterization of a Novel Human Ceramidase," *J. Biol. Chem.* 276(28):26577-26588 (2001).
Marquass et al., "Matrix-Associated Implantation of Predifferentiated Mesenchymal Stem Cells Versus Articular Chondrocytes," In Vivo Results of Cartilage Repair After 1 Year, *The American Journal of Sports Medicine* 39(7):1401-1412 (2011).
Medline Plus Online Dictionary; Definition for "embryo".
Mielke et al., "Alterations of the Sphingolipid Pathway in Alzheimer's Disease: New Biomarkers and Treatment Targets?," *Neuromol. Med.* 12:331-340 (2010).
Monick et al., "Cooperative Prosurvival Activity by ERK and Akt in Human Alveolar Macrophages is Dependent on High Levels of Acid Ceramidase Activity," J. Immunol. 173:123-35 (2004).
Morita et al., "Oocyte Apoptosis is Suppressed by Disruption of the Acid Sphingomyelinase Gene or by Sphingosine-1-Phosphate Therapy," *Nat. Med.* 6(10):1109-14 (2000).
Naslavsky et al., "Characterization of a Nonclathrin Endocytic Pathway: Membrane Cargo and Lipid Requirements," *Mol. Biol. Cell.* 15:3542-3552 (2004).
Nejadnik et al., "Autologous Bone Marrow-Derived Mesenchymal Stem Cells Versus Autologous Chondrocyte Implantation: An Observational Cohort Study," *The American Journal of Sports Medicine* 38(6):1110-1116 (2010).
Nichols et al., "Endocytosis Without Clathrin Coats," *Trends in Cell Biol.* 11(10):406-412 (2001).
Office Action for Canadian Patent Application No. 2,674,849 (dated Feb. 4, 2015).
Okino et al., "The Reverse Activity of Human Acid Ceramidase," *J. Biol. Chem.* 278(32):29948-53 (2003).
Pandey et al., "Recent Advances in the Immunology of Ceramide," *Exp. Mol. Pathol.* 82:298-309 (2007) (E-pub Oct. 12, 2006).
Park & Schuchman, "Acid Ceramidase and Human Disease," *Biochim. Biophys. Acta* 1758:2133-38 (2006).
Park et al., "Ceramide, A Crucial Functional Lipid and Its Metabolic Regulation by Acid Ceramidase," *Food Science & Biotechnology* 19(4):859-864 (2010).
Partial Supplementary European Search Report for European Patent Application No. 12830086.0 (dated Mar. 5, 2015).
Partial Supplementary European Search Report for European Patent Application No. 12803458.4 (dated Dec. 1, 2014).
Pasqualotto et al., "Effect of Oxidative Stress in Follicular Fluid on the Outcome of Assisted Reproductive Procedures," *Fertility and Sterility* 81(4):973-76 (2004).
Patrizio et al., "Molecular Methods for Selection of the Ideal Oocyte," *Reproductive BioMedicine Online* 15(3):346-53 (2007).
Perez et al., "A Central Role for Ceramide in the Age-Related Acceleration of Apoptosis in the Female Germline," *FASEB J.* 19(7):860-2 (2005).
Ramsubir et al., "In Vivo Delivery of Human Acid Ceramidase Via Cord Blood Transplantation and Direct Injection of Lentivirus as Novel Treatment Approaches for Farber Disease," *Molecular Genetics and Metabolism* 95:133-141 (2008).
Rienzi et al., "Predictive Value of Oocyte Morphology in Human IVF: A Systematic Review of the Literature," *Hum. Reprod. Update* 17(1):33-45 (2011).
Romiti et al., "Neutral/Alkaline and Acid Ceramidase Activities Are Actively Released by Murine Endothelial Cells," *Biochem. Biophys. Res. Comm.* 275:746-51 (2000).
Roudebush et al, "Embryonic Platelet-Activating Factor: An Indicator of Embryo Viability," *Hum. Reprod.* 17(5):1306-10 (2002).
Schuchman et al., "A Novel Use for Acid Ceramidase in Cell-Based Therapies for Degenerative Joint Diseases, Including the Mucopolysaccharidoses," *Molecular Genetics and Metabolism* 105:S56 (2012) (abstract only).
Schuchman et al., "Pentosan Polysulfate: A Novel Therapy for the Mucopolysaccharidoses," *PLOS One* 8(1):e54459.
Second Office Action and English Translation for Chinese Patent Application No. 201280037341.5 (mailed Nov. 3, 2015).

(56) References Cited

OTHER PUBLICATIONS

Seelan et al., "Human Acid Ceramidase is Overexpressed but Not Mutated in Prostate Cancer," *Genes Chromosomes & Cancer* 29:137 (2000).
Ségui et al., "Stress-Induced Apoptosis is Not Mediated by Endolysosomal Ceramide," *FASEB J.* 14:36-47 (2000).
Seli et al., "Noninvasive Metabolomic Profiling of Embryo Culture Media Using Proton Nuclear Magnetic Resonance Correlates With Reproductive Potential of Embryos in Women Undergoing in vitro fertilization," *Fertil. Steril.* 90:2183-89 (2008).
Sen et al., "Developments in Directed Evolution for Improving Enzyme Functions," *Appl. Biochem. Biotechnol.* 143:212-223 (2007).
Shtraizent et al., "Autoproteolytic Cleavage and Activation of Human Acid Ceramidase," *J. Biol. Chem.* 283(17):11253-9 (2008).
Simonaro et al., "Acid Ceramidase Improves the Chondrogenic Phenotype of Primary and Mesenchymal Stem Cell-Derived Chondrocytes: Implications for Cartilage Repair," *Osteoarthritis and Cartilage* 19(S1):S114-S115 (2011).
Simonaro et al., "Acid Ceramidase Maintains the Chondrogenic Phenotype of Expanded Primary Chondrocytes and Improves the Chondrogenic Differentiation of Bone Marrow-Derived Mesenchymal Stem Cells," *PLOS One* 8(4):e62715 (2013).
Simonaro et al., "Involvement of the Toll-like Receptor 4 Pathway and Use of TNF-alpha Antagonists for Treatment of the Mucopolysaccharidoses," *PNAS* 107(1):222-227 (2010).
Strelow et al., "Overexpression of Acid Ceramidase Protects from Tumor Necrosis Factor-Induced Cell Death," *J. Exp. Med.* 192(5):601-11 (2000).
Supplementary European Search Report for European Patent Application No. 13797635.3 (dated Jan. 22, 2016).
Teichgraber et al., "Ceramide Accumulation Mediates Inflammation, Cell Death and Infection Susceptibility in Cystic Fibrosis," *Nat. Med.* 14(4):382-391 and Supplementary Information (2008).
Thon et al., "The Murine TRAIL Receptor Signals Caspase-Independent Cell Death Through Ceramide," *Experimental Cell Research* 312:3808-21 (2006).
UniProt_D7BW40 (last modified Aug. 10, 2010).
UniProt_Q19784 ( last modified Sep. 11, 2007).
UniProt_Q8YUN7 (last modified Mar. 1, 2002).
Walia et al., "Autologous Transplantation of Lentivector/Acid Ceramidase-Transduced Hematopoietic Cells in Nonhuman Primates," *Human Gene Therapy* 22:679-687 (2011).
Weinreb et al., "Effectiveness of Enzyme Replacement Therapy in 1028 Patients with Type 1 Gaucher Disease After 2 to 5 Years of Treatment: A Report from the Gaucher Registry," *Am. J. Med.* 113:112-19 (2002).
Whisstock et al., "Prediction of Protein Function from Protein Sequence," *Q. Rev. Biophysics* 36(3):307-340 (2003).
Wishart et al., "A Single Mutation Converts a Novel Phosphotyrosine Binding Domain Into a Dual-Specificity Phosphatase," *J. Biol. Chem.* 270(45):26782-26785 (1995).
Witkowski et al., "Conversion of b-ketoacyl Synthase to a Malonyl Decarboxylase by Replacement of the Active Cysteine With Glutamine," *Biochemistry* 38:11643-11650 (1999).
Witsenburg et al., "Cumulative Live Birth Rates in Cohorts of Patients Treated With in Vitro Fertilization or Intracytoplasmic Sperm Injection," *Fertil. Steril.* 84(1):99-107 (2005).
Xu et al., "Golgi Alkaline Ceramidase Regulates Cell Proliferation and Survival by Controlling Levels of Sphingosine and SIP," *The FASEB Journal* 20:1813-25 (2006).
Young et al., "Sphingolipids: Regulators of Crosstalk Between Apoptosis and Autophagy," *J. Lipid. Res.* 54:5-19 (2013).
Office Action for European Application No. 12803458.4 (Feb. 8, 2016).
English Translation and Notice of Reasons for Rejection for Japanese Patent Application No. 2014-517125 (Dec. 12, 2016).
Grassmé et al., "Rhinoviruses Infect Human Epithelial Cells via Ceramide-Enriched Membrane Platforms," J. of Biological Chemistry 280(28)(Issue of Jul. 15):26256-26262 (2005).
Gassert et al., "Induction of Membrane Ceramides: A Novel Strategy to Interfere with T Lymphocyte Cytoskeletal Reorganization in Viral Immunosuppression," *PLoS Pathogens* 5(10):1-11 (2009).
Gulbins et al., "Ceramide, Membrane Rafts and Infections," J. Mol. Med. 82:357-363 (2004).
Simons et al., "Cholesterol, Lipid Rafts, and Disease," J. of Clinical Investigation 110(5):597-603 (2002).
Becker et al., "Ceramide in Pseudomonas aeruginosa Infections and Cystic Fibrosis," Cell Physiol. Biochem. 26:57-66 (2010).
Esen et al., "Mechanisms of *Staphylococcus aureus* Induced Apoptosis of Human Endothelial Cells," Apoptosis 6 (6):431-439 (2001).
Grassmé et al., "Acidic Sphingomyelinase Mediates Entry of N. gonorrhoeae into Nonphagocytic Cells," Cell 31:605-615 (1997).
Grassmé et al., "Host Defense Against Pseudomonas aeruginosa Requires Cermaide-Rich Membrane Rafts," Nature Medicine 9(3):322-330 (2003).
Dreschers et al., "Infections with Human Rhinovirus Induce the Formation of Distinct Functional Membrane Domains," Dell Physiol. Biochem. 20:241-254 (2007).
English Translation and Notice of Reasons for Rejection for Japanese Application No. 2014-517125 (May 9, 2016).
Supplementary European Search Report and European Search Opinion for European Application 14775400.6 (Jun. 27, 2016).
English Translation and Office Action for Chinese Application No. 201280037341.5 (dated Jul. 26, 2016).
Restriction Requirement for U.S. Appl. No. 14/776,442 (Aug. 26, 2016).
Office Action for U.S Appl. No. 14/776,442 (Dec. 9, 2016).
Office Action for U.S. Appl. No. 14/343,150 (dated Feb. 27, 2017).
Gilbert et al., "Exogenous Sphingomyelinase Increases Collagen and Sulphated Glycosaminoglycan Production by Primary Articular Chondrocytes: An in Vitro Study," Arthritis Research & Therapy 8(4):R89 (2006).
English Translation and Notice of Reasons for Rejection of Japanese Patent Application No. 2015-515238 (dated Mar. 6, 2017).
Seikagaku, "Metabolism of Sphingolipids Centered on Ceramide," Biochemistry 83(6):495-505 (2011) (English abstract only).
English Translation and Fourth Office Action for Chinese Patent Application No. 201280037341.5 (mailed Mar. 20, 2017)
English Translation and Second Office Action for Chinese Patent Application No. 201380031825.3 (mailed Apr. 6, 2017).

* cited by examiner

TARGETED PROTEIN REPLACEMENT FOR THE TREATMENT OF LYSOSOMAL STORAGE DISORDERS

This application is a continuation of U.S. application Ser. No. 11/631,248, now U.S. Pat. No. 8,889,127, which is a national stage of international application no. PCT/US2005/023529 filed on Jul. 1, 2005, which claims the benefit of the U.S. provisional application No. 60/584,648 filed on Jul. 1, 2004, each of which is incorporated by reference herein in its entirety.

This invention was made with government support under grant numbers HD 28607 and HL/GM 71175-01, both awarded by the National Institutes of Health, and PR 012262, awarded by the Department of Defense. The government has certain rights in the invention.

1. FIELD OF THE INVENTION

The present invention relates to compositions and methods for delivering lysosomal proteins. The compositions and methods described herein permit the targeted delivery of exogenous lysosomal proteins to cell surface proteins that allow their internalization via non-clathrin pathways. The present invention further relates to the use of the compositions and methods for enzyme replacement therapy of lysosomal storage diseases.

2. BACKGROUND OF THE INVENTION

Inherited deficiency of human lysosomal proteins (including hydrolases, transport proteins, receptor molecules, ion pumps, and small "activator" molecules) leads to lysosomal storage disorders or LSD (Hers, 1963, Biochem. J. 86:11-16; Scriver et al., 2000, The Metabolic and Molecular Bases of Inherited Disease, 8th ed., McGraw-Hill), one of the most prevalent genetic defects, affecting one out of seven thousand live births (Meikle et al., 1999, JAMA 281:249-254). More than 40 forms of LSD have been identified in humans. Their manifestations include accumulation of non-degraded substrates, lysosomal engorgement, cell damage and tissue dysfunction (e.g., neuropathy, pulmonary, renal, and hepatic disorders), increased morbidity, and premature mortality (Reviewed by Scriver et al., 2000, The Metabolic and Molecular Bases of Inherited Disease, 8th ed., McGraw-Hill).

Current therapies, limited to symptomatic palliative treatment, only very marginally improve LSD prognosis (Scriver et al., 2000, The Metabolic and Molecular Bases of Inherited Disease, 8th ed., McGraw-Hill). New approaches are focused on gene therapy and transplantation of lysosomal protein-secreting cells or bone marrow stem cells (Malatack et al., 2003, Pediatr. Neurol. 29:391-403; Krivit et al., 1992, Bone Marrow Transplant. 10(Suppl. 1):87-96; Haskins, 1996, Bone Marrow Transplant. 18(Suppl. 3):S25-S27; Jin et al., 2003, Mol. Ther. 8:876-885; Miranda et al., 2000, Gene Ther. 7:1768-1776; Miranda et al., 1998, Transplantation 65:884-892; Leimig et al., 2002, Blood 99:3169-3178; Hoogerbrugge et al., 1988, J. Clin. Invest. 81:1790-1794; Yeyati et al., 1995, Hum. Gene Ther. 6:975-983). However, practicality of gene therapies is limited by abnormal processing of newly synthesized lysosomal proteins achieved by gene transfection and general concerns on safety and effectiveness of this strategy (D'Azzo, 2003, Acta Haematol. 110:71-85; Cabrera-Salazar et al., 2002, Curr. Opin. Mol. Ther. 4:349-358; Taylor et al., 1997, Nature Med. 3:771-774). Lack of compatible donors, risk of body irradiation and immunosuppressive agents and graft-versus-host diseases hinder applicability of transplantation (Estruch et al., 2001, J. Gene Med. 3:488-497; Miranda et al., 1997, Blood 90:444-452; Vellodi et al., 1997, Arch. Dis. Child. 76:92-99; Miranda et al., 2000, Faseb J. 14:1988-1995; Jin et al., 2002, J. Clin. Invest. 109:1183-1191).

At the present time, protein replacement therapy seems to be the most feasible treatment, in particular in the case of non-neurological LSD (e.g., Gaucher I, Fabry disease, Niemann-Pick B (Reviewed by Brady, 2003, Phil. Trans. R. Soc. London B Biol. Sci. 358:915-919; Grabowski and Hopkin, 2003, Annu. Rev. Genomics Hum. Genet. 4:403-436; Desnick and Schuchman, 2002, Nature Rev. Genet. 3:954-966; Barton et al., 1990, Proc. Natl. Acad. Sci. USA 87:1913-1916; LeBowitz et al., 2004, Proc. Natl. Acad. Sci. USA 101:3083-3088). The principle of LSD therapy by infusion of exogenous proteins is based on the phenomenon that endogenous human lysosomal proteins (e.g., enzymes such as hydrolases that needed to be replaced) are normally modified with mannose and/or mannose-6-phosphate (M6P) residues and, therefore, can bind to cellular mannose or M6P receptors (MR, M6PR), followed by internalization via clathrin-mediated pathways and rapid trafficking to lysosomes (Kaplan et al., 1977, Proc. Natl. Acad. Sci. USA 74:2026-2030; Kornfeld et al., 1982, CIBA Found. Symp. (92):138-156).

Given these specific glycosylation requirements, production of recombinant proteins for the treatment of LSD cannot take advantage of typical expression systems (e.g., bacteria, yeast, or insect cells), but these proteins must be produced in mammalian cells (Boose et al., 1991, Glycobiology 1:295-305). Nevertheless, even when produced in mammalian systems (e.g., CHO cells), some lysosomal proteins are poorly or differently modified (Waheed et al., 1988, EMBO J. 7:2351-2358; He et al., 1999, Biochim. Biophys. Acta 1432:251-264; Miranda et al., 2000, FASEB J. 14:1988-1995; Zhu et al., 2004, J. Pharmacol. Exp. Ther. 308:705-711), thus lack of mannose residues or accessibility of these for receptor binding are common obstacles affecting the targeting capacity of recombinant lysosomal proteins (Murray, 1987, Meth. Enzymol. 149:25-42).

Strategies to overcome this problem focused on increasing effective exposure of mannose residues by in vitro modification of the lysosomal proteins (e.g., digestion of oligosaccharide side chains) (Murray, 1987, Meth. Enzymol. 149:25-42; Furbish et al., 1981, Biochim. Biophys. Acta 673:425-434; Brady et al., 1994, J. Inherit. Metab. Dis. 17:510-519). Moreover, augmentation of the dose of the infused proteins has been utilized to compensate for their relative targeting inefficiency, but this strategy will likely result in detrimental side effects (e.g., immunogenic responses), together with rapid saturation of the receptor-mediated uptake (Mistry et al., 1996, Lancet 348:1555-1559; Friedman et al., 1999, Blood 93:2807-2816). Alternative means to enhance the efficiency of enzyme replacement therapy for LSD included administration of dexamethasone, to increase the density of surface MR (Zhu et al., 2004, J. Pharmacol. Exp. Ther. 308:705-711). However, protein delivery to MR, preferentially expressed in the reticulo-endothelial system (RES), precludes other cells and tissues from being efficiently targeted (Stahl et al., 1978, Proc. Natl. Acad. Sci. USA 75:1399-1403; Achord et al., 1978, Cell 15:269-278).

Related receptors used by endogenous lysosomal proteins, namely M6PR (cation-independent and cation-dependent receptors), can be utilized to deliver the infused recombinant proteins to cell types other than RES (Kornfeld, 1990, Biochem. Soc. Trans. 18:367-374; Kornfeld, 1987, FASEB J. 1:462-468; Sands et al., 2001, J. Biol. Chem. 276:43160-43165). Nevertheless, also lack of M6P residues in recombinant lysosomal proteins leads to rapid clearance of these from the circulation (He et al., 1999, Biochim. Biophys. Acta 1432:251-264). To circumvent this obstacle, a recent work focused on targeting of a recombinant lysosomal protein (e.g., β-glucoronidase) in a glycosylation-independent manner, by generating a fusion protein tagged with a peptide derived from the insulin-like growth factor II (IGF II), which acts per se as a ligand for M6PR (LeBowitz et al., 2004, Proc. Natl. Acad. Sci. USA 101:3083-3088). However, in contrast to control cells, recent evidence showed defective internalization via clathrin-mediated pathways in LSD cells, which may also hinder this strategy (Dhami et al., 2004, J. Biol. Chem. 279:1526-1532; Prince et al., 2004, J Biol Chem. 279(33):35037-46).

To circumvent this obstacle, two recent works focused on targeting of recombinant lysosomal enzymes (β-glucoronidase, alpha-L-iduronidase and acid alpha-glucosidase) in a glycosylation-independent manner, by generating fusion proteins tagged with: i) a peptide derived from the insulin-like growth factor II (IGF II), which acts per se as a ligand for M6PR (LeBowitz et al., 2004, Proc. Natl. Acad. Sci. USA 101:3083-3088); or ii) a peptide derived from receptor associated protein, RAP, which binds to several LDL receptor family members (Prince et al., 2004, J Biol Chem. 279(33):35037-46). However, both these targets are internalized within cells by clathrin-mediated pathways, which are defective in LSD cells, also hindering the efficacy of this strategy (Dhami et al., 2004, J. Biol. Chem. 279:1526-1532; Section 6.4 below).

Therefore, effective intracellular delivery of injected lysosomal proteins to their ultimate target, lysosomes, has not been achieved by known formulations and methods for enzyme replacement therapy.

Discussion or citation of a reference herein shall not be construed as an admission that such reference is prior art to the present invention.

3. SUMMARY OF THE INVENTION

Enzyme replacement therapy (ERT) for lysosomal storage disorders (LSDs) relies on the uptake of recombinant enzymes injected in circulation by cell surface receptors (i.e., mannose or mannose 6 phosphate receptors, MR and M6PR) which recognize sugar residues on the recombinant enzymes (mannose or M6P), mediating internalization by clathrin-mediated pathways and lysosomal delivery lysosomes (Kaplan et al., 1977, Proc. Natl. Acad. Sci. USA 74:2026-2030; Kornfeld et al., 1982, CIBA Found. Symp. (92):138-156).

However, despite the presence of M6P residues in a recombinant lysosomal enzyme, acid sphigomyelinase (ASM), which is deficient in types A and B Niemann-Pick Disease (NPD), a recent work showed that internalization of ASM by cells derived from ASM knockout mice was markedly reduced when compared with normal cells (Dhami et al., J. Biol. Chem. 279:1526-1532). Results in this study suggested that recombinant ASM was taken up by a combination of MR and M6PR in control cells, whereas in the deficient cells the M6PR had a minimal role in uptake, suggesting that lipid accumulation in deficient cells lead to abnormalities in M6PR endocytosis/trafficking. Studies presented herein (see Section 6.4 below) indicate that deficiencies in clathrin-mediated trafficking exist in other lysosomal storage diseases.

The present invention is based, at least in part, on the discovery that ASM, as an exemplary lysosomal protein, can be efficiently delivered to lysosomes in a clathrin-independent mechanism when coupled to suitable targeting moieties.

Thus, in certain aspects, the present invention provides mammalian lysosomal proteins, or active fragments thereof, that are attached to a targeting moiety, wherein the targeting moiety binds to a mammalian cell surface molecule and allows internalization of said mammalian lysosomal protein or active fragment by the mammalian cell via a non-clathrin pathway.

In certain embodiments, the mammalian lysosomal protein or active fragment is covalently attached to said targeting moiety and said protein or said fragment; in other embodiments, the mammalian lysosomal protein or active fragment is a fusion protein comprising the targeting moiety and the lysosomal protein or fragment (at the N-terminus, C-terminus, or both termini).

Thus, in some embodiments, the mammalian lysosomal protein or active fragment is conjugated to the targeting moiety, for example through chemical or photo-crosslinking.

The targeting moiety attached to the mammalian lysosomal protein or active fragment can be an antibody or another, non-immunoglobulin polypeptide.

Preferably, the targeting moiety binds to an extracellular portion of ICAM-1 or PECAM-1. In a most preferred embodiment, the targeting moiety binds to an extracellular portion of ICAM-1, for example, is an antibody against ICAM-1.

In certain embodiments, the mammalian lysosomal protein or active fragment is purified, for example is at least 50%, 60%, 70%, 75%, 80%, 85%, 90%, 95%, or 98% pure.

The present invention further provides particles comprising the mammalian lysosomal proteins and/or active fragments of the invention.

In certain embodiments, the particles range from 50 nm to 10 μm in size, and are preferably 200-300 nm in size.

The particles can be synthetic carrier particle useful for delivery of the lysosomal proteins and/or active fragments to a subject, such as, for example, a liposome, a microbubble, a dendrimer, a polymerosome, or a micelle. In certain embodiments, the synthetic carrier particle is coupled to, loaded into, loaded onto or coated with the targeting moiety.

The present invention further provides pharmaceutical compositions comprising (a) the lysosomal proteins, active fragments and/or particles of the invention and (b) a pharmaceutically acceptable carrier, and methods of treating a subject in need of lysosomal protein replacement therapy by administering to said subject a therapeutically effective amount of such pharmaceutical compositions.

Any lysosomal storage disease can be treated by the methods of the invention, including, but not limited to, Pompe Disease, GM1 gangliosidosis, Tay-Sachs disease, GM2 gangliosidosis, Sandhoff disease, Fabry disease, Gaucher disease, metachromatic leukodystrophy, Krabbe disease, Niemann-Pick disease type A, Niemann-Pick disease type B, Niemann-Pick disease type C, Niemann-Pick disease type D, Farber disease, Wolman disease, Hurler Syndrome, Scheie Syndrome, Hurler-Scheie Syndrome, Hunter Syndrome, Sanfilippo A Syndrome, Sanfilippo B Syndrome, Sanfilippo C Syndrome, Sanfilippo D Syndrome, Morquio A disease, Morquio B disease, Maroteaux-Lamy disease, Sly Syndrome, α-mannosidosis, β-mannosidosis, fucosidosis, aspartylglucosaminuria, sialidosis, mucolipidosis II, mucolipidosis III, mucolipidosis IV, Goldberg Syndrorme, Schindler disease, cystinosis, Salla disease, infantile sialic acid storage disease, Batten disease, infantile neuronal ceroid lipofuscinosis, or prosaposin.

The present invention further provides nucleic acids comprising nucleotide sequences encoding fusion proteins of the mammalian lysosomal proteins or their active fragment and the targeting moeities. The nucleotide sequences are preferably operably linked to promoters and/or origins of replication.

The present invention further provides recombinant cells which comprise, either in their genome or on an extrachromosomal replicable nucleic acid (e.g., a plasmid or a YAC) a nucleic acid encoding encoding fusion proteins of the mammalian lysosomal proteins or their active fragment and the targeting moeities. In certain embodiments, the recombinant cells are mammalian cells in culture.

The present invention provides methods for producing the mammalian lysosomal protein or active fragment of the invention, comprising (a) culturing a recombinant cell comprising a nucleic acid encoding fusion proteins of the mammalian lysosomal proteins or their active fragment and the targeting moeities under conditions in which the fusion proteins expressed; and (b) recovering the expressed fusion proteins.

The present methods and compositions relate to any mammalian lysosomal protein (or active fragment), for example α-N-acetylgalactosaminidase, acid lipase, α-galactosidase, glucocerebrosidase, α-L-iduronidase, iduronate sulfatase, α-mannosidase, α-L-fucosidase, sialidase, or acid sphingomyelinase.

4. BRIEF DESCRIPTION OF THE FIGURES

FIG. 1A-1C. Size and activity of anti-ICAM/ASM conjugates. FIG. 1A. Anti-ICAM/ASM conjugates were prepared by direct absortion of both anti-ICAM antibody and ASM enzymatic cargo to the surface of latex beads, or by biotinylation of antibody and enzyme, followed by streptavidin crosslinking. FIG. 1B. Determination of anti-ICAM/ASM conjugate size by dynamic light scattering, showing internalizable-size conjugates (113 nm in diameter). FIG. 1C. Comparative analysis of ASM activity (by Amplex Red-sphingomyelinase assay) in control anti-ICAM conjugates or anti-ICAM/ASM conjugates.

Figures 2A, 2B:
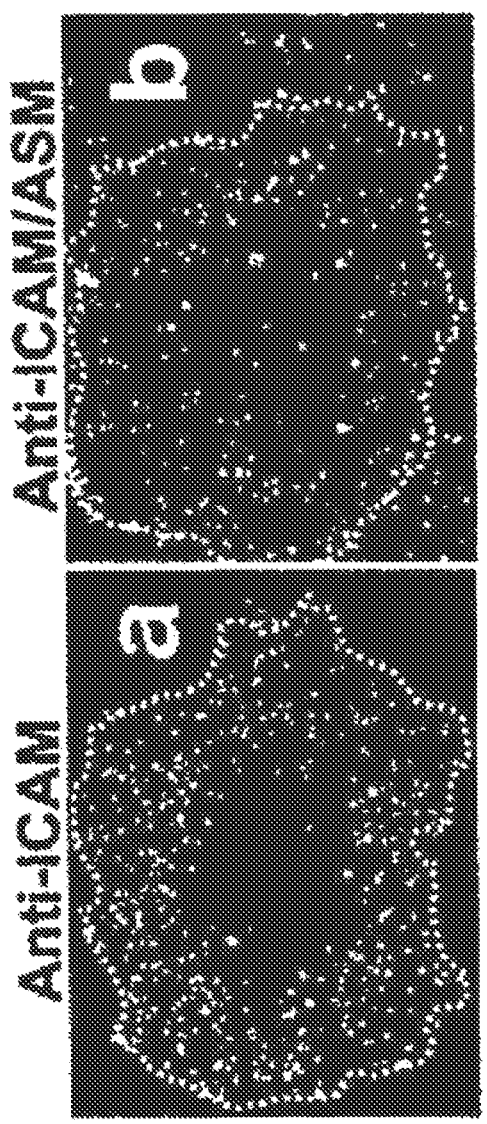

FIG. 2A-2B. Binding of anti-ICAM/ASM conjugates to endothelial cells ("EC"). TNF-α activated HUVEC were incubated for 30 min at 4° C. in the presence of fluorescently-labeled control anti-ICAM conjugates (FIG. 2A) or anti-ICAM/ASM conjugates (FIG. 2B), to permit binding to the target. EC were washed, fixed, and analyzed by fluorescence microscopy. EC borders are marked by a dashed line.

Figures 3A, 3B, 3C, 3D:
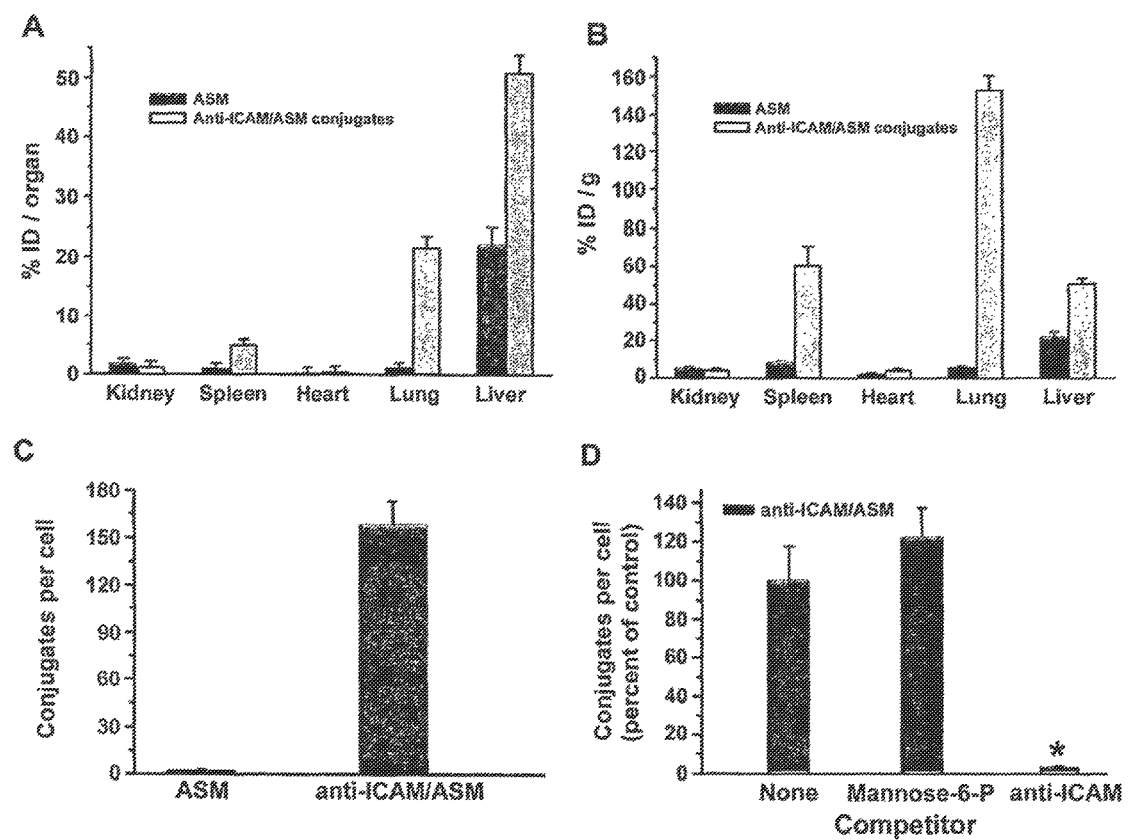

FIG. 3A-3D. Biodistribution and targeting specificity of anti-ICAM/ASM conjugates. FIG. 3A. Total organ delivery capacity of 125I-labeled ASM, either untargeted or targeted to ICAM-1, injected IV into anesthetized C57BI/6 mice (% ID/organ=percent of injected dose per organ). FIG. 3B. Organ specificity of 125I-ASM or anti-ICAM/125I-ASM conjugates (% ID/g=percent of injected dose per gram of organ). FIG. 3C. Capacity of green-fluorescent ASM conjugates or anti-ICAM/ASM conjugates to bind to HUVEC at 4° C. for 30 min. After incubation with the cells, non-internalized conjugates were stained with a secondary antibody labeled in red. Thus, surface-bound conjugates were detected as yellow color vs internalized conjugates, detected as green color. The images were analyzed by fluorescence microscopy and automatically quantified to determine the number of conjugates per cell. FIG. 3D. Binding of anti-ICAM/ASM conjugates to HUVEC was determined as above in the presence of either control medium or medium supplemented with mannose 6 phosphate or free anti-ICAM-1, to compete for conjugate binding.

Figures 4A, 4B, 4C, 4D:
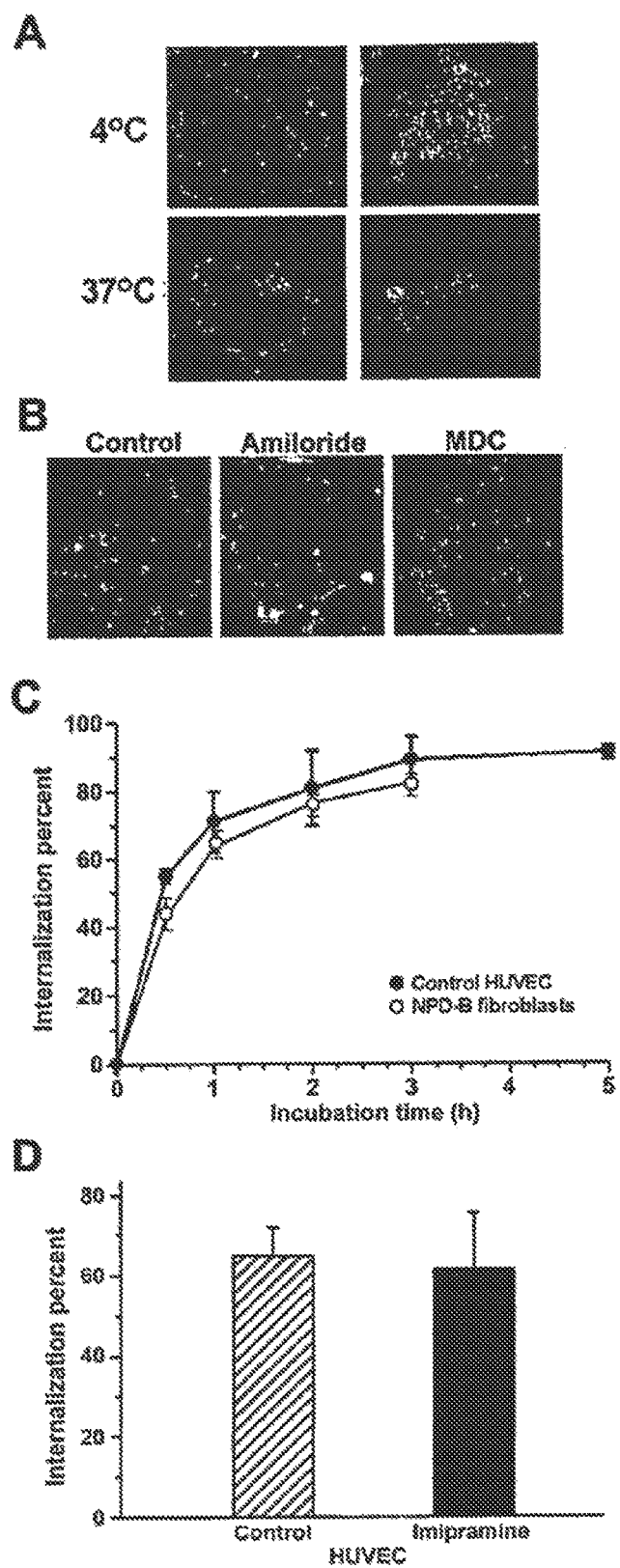

FIG. 4A-4D. Intracellular delivery of anti-ICAM/ASM conjugates. FIG. 4A. Intracellular delivery of green-fluorescent anti-ICAM/ASM conjugates in HUVEC was determined at both 4° C. and 37° C. (2 h incubation). Non-internalized conjugates were counterstained as described in FIG. 3C, thus yellow conjugates are located at the cell surface whereas green conjugates are internalized within the cells. FIG. 4B. Estimation of the internalization capacity of anti-ICAM/ASM conjugates within HUVEC treated with either control medium or medium containing specific endocytic inhibitors (3 mM amiloride inhibits ICAM-mediated internalization, 50 µM MDC inhibits clathrin-mediated uptake), where yellow color represent non-internalized conjugates (1 h incubation). FIG. 4C. The internalization capacity of anti-ICAM/ASM conjugates was estimated as the percent of conjugates internalized respect to the total amount of conjugates associated to the cells, at varying periods of time. A comparison of the internalization kinetics in HUVEC and skin fibroblast from a Niemann-Pick patient is shown. FIG. 4D. Comparison of the internalization capacity of anti-ICAM/ASM conjugates in control HUVEC or HUVEC treated with the ASM inhibitor, 50 µM imipramine (2 h incubation).

Figure 5:
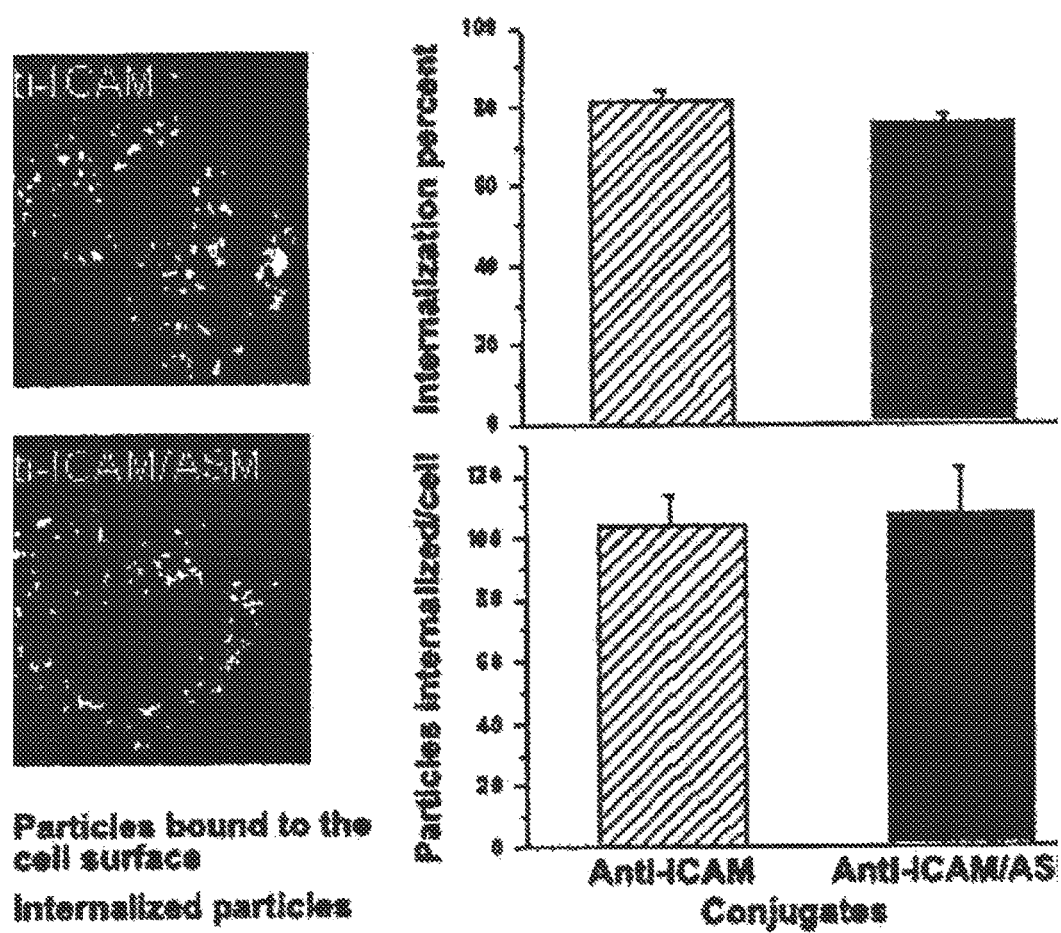

FIG. 5. Internalization of anti-ICAM/ASM conjugates in endothelial cells. Activated HUVEC were incubated for 1 h at 37° C. in the presence of FITC-labeled control anti-ICAM or anti-ICAM/ASM conjugates, to permit endocytosis. The cells were washed, fixed and stained with TexasRed goat anti-mouse IgG, to label conjugates bound to the cell surface. The samples were analyzed by fluorescence microscopy and automatically quantified to determine the uptake capacity (number of conjugates internalized per cell) and efficiency (internalized conjugates versus surface-bound conjugates).

Figures 6A, 6B, 6C:
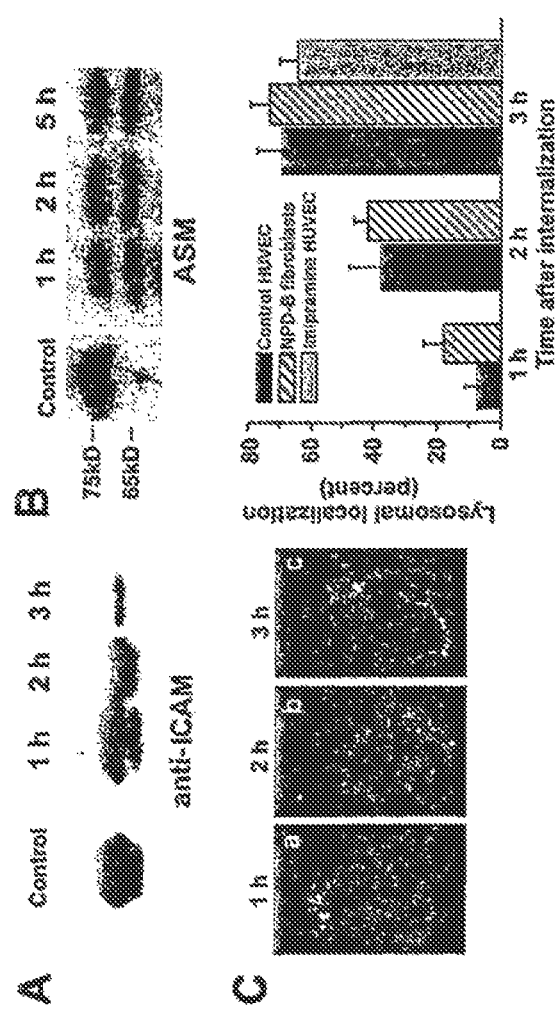

FIG. 6A-6C. Stability and lysosomal trafficking of anti-ICAM/ASM conjugates. HUVEC were incubated with either $^{125}$I-anti-ICAM/ASM conjugates (FIG. 6A) or anti-ICAM/$^{125}$I-ASM conjugates (FIG. 6B) for 30 min at 4° C. to permit binding. The cells were then washed and warmed to 37° C. to permit internalization for varying periods of time. The cells were lysed, total cell protein was determined, and comparable amounts of cell lysates were separated in a 10% SDS-PAGE and blotted to a nytrocellulose membrane. The protein bands were visualized by exposing an X-ray film to the radioblot. FIG. 6C. Colocalization of green-fluorescent anti-ICAM/ASM conjugates with Texas Red dextran-labeled lysosomal compartments in HUVEC (shown as yellow color) at varying time periods after internalization. Merged imaged were automatically quantified to determined the percent of conjugates that trafficked to lysosomes in either control HUVEC, NPD-B fibroblasts or imipramine-treated HUVEC.

Figures 7A, 7B:
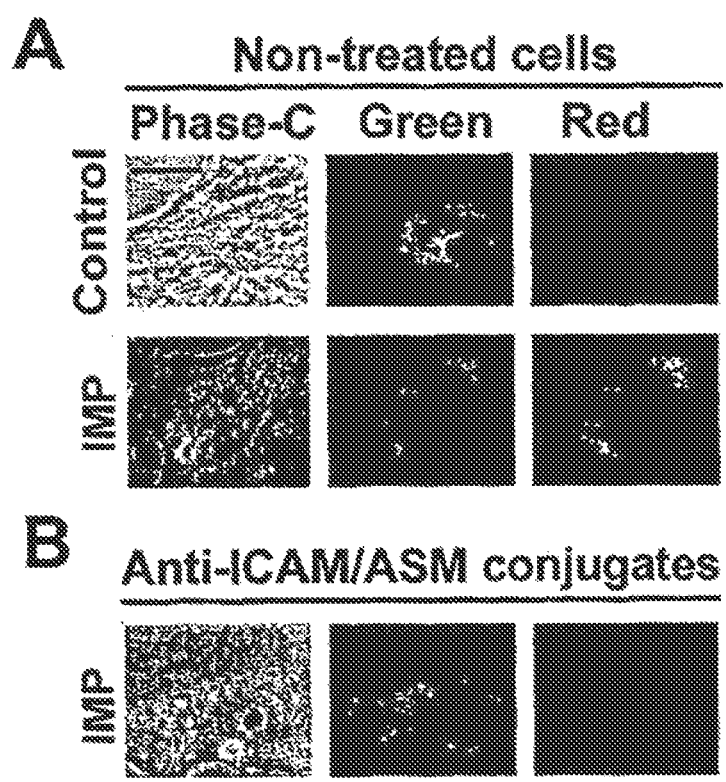

FIG. 7A-7B. Therapeutic activity of ASM delivered to lysosomes by anti-ICAM conjugates. FIG. 7A. HUVEC were incubated overnight with BODIPY-FLC12-sphingomyelin in the presence or absence of 50 µM imipramine (IMP), which degrades endogenous ASM. Cells were washed, fixed, and analyzed by fluorescent microscopy. Control HUVEC showed green fluorescence in lysosomes and Golgi, reflecting low levels of the fluorochrome, whereas high concentration of BODIPY-FLC12-sphingomyelin was visualized in lysosomes under the red channel in IMP-treated cells. FIG. 7B. Aberrant BODIPY-FLC12- sphingomyelin concentration in lysosomes of IMP-treated HUVEC was reverted by treatment of the cells with anti-ICAM/ASM conjugates for 3 h at 37° C.

Figures 8A, 8B:
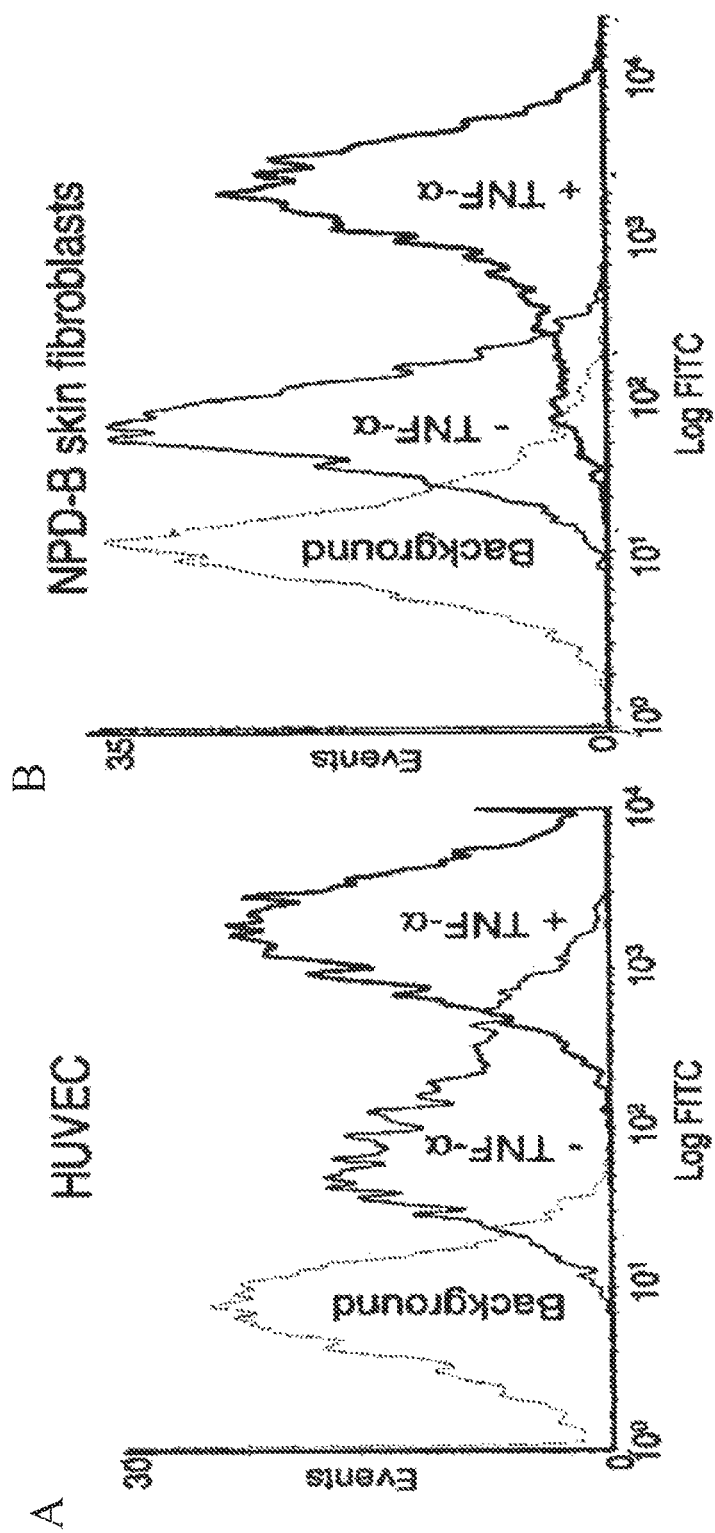

FIG. 8A-8B. Expression of ICAM-1 in NPD-B skin fibroblasts. Skin fibroblast from NPD-B patients were subjected to FACS analysis using anti-human ICAM-1. As in the case of HUVEC, the patient-derived cell type expressed surface accessible ICAM-1, which was up-regulated in pro-inflammatory conditions (TNF-α).

DETAILED DESCRIPTION OF THE INVENTION

5.1 Lysosomal Proteins

Lysosomal proteins, including lysosomal enzymes, and functionally active fragments, derivatives, and variants thereof are collectively referred to herein as "lysosomal proteins of the invention" or, simply, "proteins of the invention." Nucleic acid molecules encoding the proteins of the invention are collectively referred to as "nucleic acids of the invention."

Thus, the lysosomal protein useful for practicing the invention can be a naturally-occurring lysosomal protein or modified lysosomal protein that is enzymatically active, for example a protein that comprises: (a) an enzymatically-active fragment of a mammalian lysosomal protein of interest; (b) a protein having one or more amino acid residues added to the amino or carboxyl terminus of the mammalian lysosomal protein, including but not limited to a targeting moiety; and/or (c) a protein having one or more naturally-occurring amino acid additions, deletions or substitutions relative to the mammalian lysosomal protein of interest. In certain embodiments, the modified lysosomal protein can comprise a signal peptide or detectable marker peptide at the amino or carboxyl terminal.

One aspect of the invention pertains to isolated lysosomal proteins, including biologically active portions (e.g., enzymatically active portions where the protein is an enzyme) thereof. In certain, non-limiting embodiments, the lysosomal protein is α-N-acetylgalactosaminidase, acid lipase, α-galactosidase, glucocerebrosidase, α-L-iduronidase, iduronate sulfatase, α-mannosidase, α-L-fucosidase, sialidase, or acid sphingomyelinase.

The sequences of mRNA encoding mammalian lysosomal proteins, and their encoded proteins, are well known in the art. By way of example but not limitation, Genbank sequence accession nos. for the mRNAs of exemplary human lysosomal proteins and their mRNAs are provided herein: acid sphingomyelinase (ASM), M59916; acid lipase, M74775; α-N-acetylgalactosaminidase, M62783; α-galactosidase A, X05790; alpha-L-iduronidase, M74715; iduronate sulfatase, NM_006123 or NM_000202; sialidase, U84246; neuraminidase, AF040958; and α-mannosidase, U05572.

In one embodiment, the native lysosomal protein can be isolated from cells or tissue sources by an appropriate purification scheme using standard protein purification techniques. In another embodiment, lysosomal proteins of the invention are produced by recombinant DNA techniques. Alternative to recombinant expression, a lysosomal protein of the invention can be synthesized chemically using standard peptide synthesis techniques.

An "isolated" or "purified" protein or biologically active portion thereof is substantially free of cellular material or other contaminating proteins from the cell or tissue source from which the protein is derived, or substantially free of chemical precursors or other chemicals when chemically synthesized. The language "substantially free of cellular material" includes preparations of protein in which the protein is separated from cellular components of the cells from which it is isolated or recombinantly produced. Thus, protein that is substantially free of cellular material includes preparations of protein having less than about 30%, 20%, 10%, or 5% (by dry weight) of heterologous protein (also referred to herein as a "contaminating protein"). When the protein or biologically active portion thereof is recombinantly produced, it is also preferably substantially free of culture medium, i.e., culture medium represents less than about 20%, 10%, or 5% of the volume of the protein preparation. When the protein is produced by chemical synthesis, it is preferably substantially free of chemical precursors or other chemicals, i.e., it is separated from chemical precursors or other chemicals which are involved in the synthesis of the protein. Accordingly such preparations of the protein have less than about 30%, 20%, 10%, 5% (by dry weight) of chemical precursors or compounds other than the protein of interest.

Biologically active portions of a lysosomal protein of the invention include proteins comprising amino acid sequences sufficiently identical to or derived from the amino acid sequence of the protein, which include fewer amino acids than the full length protein, and exhibit at least one activity of the corresponding full-length protein. Moreover, other biologically active portions, in which other regions of the protein are deleted, can be prepared by recombinant techniques and evaluated for one or more of the functional activities of the native form of a lysosomal protein of the invention.

Useful lysosomal proteins are substantially identical (e.g., at least about 95%, or, more preferably at least 98% or at least 99%) to a native lysosomal protein, and retain the functional activity of the protein of the corresponding naturally-occurring protein. Such proteins can differ from the corresponding naturally-occurring protein in amino acid sequence due to natural allelic variation or mutagenesis.

To determine the percent identity of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (, % identity=# of identical positions/total # of positions (e.g., overlapping positions)×100). In one embodiment, the two sequences are the same length.

The determination of percent identity between two sequences can be accomplished using a mathematical algorithm. A preferred, non-limiting example of a mathematical algorithm utilized for the comparison of two sequences is the algorithm of Karlin and Altschul (1990) *Proc. Natl. Acad. Sci. USA* 87:2264-2268, modified as in Karlin and Altschul (1993) *Proc. Natl. Acad. Sci. USA* 90:5873-5877. Such an algorithm is incorporated into the NBLAST and XBLAST programs of Altschul, et al. (1990) *J. Mol. Biol.* 215:403-410. BLAST nucleotide searches can be performed with the NBLAST program, score=100, wordlength=12 to obtain nucleotide sequences homologous to a nucleic acid molecule of the invention. BLAST protein searches can be performed with the XBLAST program, score=50, wordlength=3 to obtain amino acid sequences homologous to a protein molecule of the invention. To obtain gapped alignments for comparison purposes, Gapped BLAST can be utilized as described in Altschul et al. (1997) *Nucleic Acids Res.* 25:3389-3402. Alternatively, PSI-Blast can be used to perform an iterated search which detects distant relationships between molecules (Id.). When utilizing BLAST, Gapped BLAST, and PSI-Blast programs, the default parameters of the respective programs (e.g., XBLAST and NBLAST) can be used.

Another preferred, non-limiting example of a mathematical algorithm utilized for the comparison of sequences is the algorithm of Myers and Miller, CABIOS (1989). Such an algorithm is incorporated into the ALIGN program (version 2.0) which is part of the CGC sequence alignment software package. When utilizing the ALIGN program for comparing amino acid sequences, a PAM120 weight residue table, a gap length penalty of 12, and a gap penalty of 4 can be used. Additional algorithms for sequence analysis are known in the art and include ADVANCE and ADAM as described in Torellis and Robotti (1994) *Comput. Appl. Biosci.,* 10:3-5; and FASTA described in Pearson and Lipman (1988) *Proc. Natl. Acad. Sci.* 85:2444-8. Within FASTA, ktup is a control option that sets the sensitivity and speed of the search. If ktup=2, similar regions in the two sequences being compared are found by looking at pairs of aligned residues; if ktup=1, single aligned amino acids are examined. ktup can be set to 2 or 1 for protein sequences, or from 1 to 6 for DNA sequences. The default if ktup is not specified is 2 for proteins and 6 for DNA.

The percent identity between two sequences can be determined using techniques similar to those described above, with or without allowing gaps. In calculating percent identity, typically exact matches are counted.

The invention also provides chimeric or fusion proteins, including but not limited to fusion proteins. As used herein, a "chimeric protein" or "fusion protein" comprises all or part (preferably biologically active) of a lysosomal protein of the invention operably linked to a heterologous protein (i.e., a protein other than the same lysosomal protein, including but not limited to a targeting moiety). Within the fusion protein, the term "operably linked" is intended to indicate that the lysosomal protein of the invention and the heterologous protein are fused in-frame to each other. The heterologous protein can be fused to the N-terminus, C-terminus or both termini of the lysosomal protein of the invention.

One useful fusion protein is a GST fusion protein in which the lysosomal protein of the invention is fused to the C-terminus of GST sequences. Such fusion proteins can facilitate the purification of a recombinant lysosomal protein of the invention.

In another embodiment, the fusion protein contains a heterologous signal sequence at its N-terminus. For example, the native signal sequence of a lysosomal protein can be removed and replaced with a signal sequence from another protein. For example, the gp67 secretory sequence of the baculovirus envelope protein can be used as a heterologous signal sequence (*Current Protocols in Molecular Biology*, Ausubel et al., eds., John Wiley & Sons, 1992). Other examples of eukaryotic heterologous signal sequences include the secretory sequences of melittin and human placental alkaline phosphatase (Stratagene; La Jolla, Calif.). In yet another example, useful prokaryotic heterologous signal sequences include the phoA secretory signal (Sambrook et al., supra) and the protein A secretory signal (Pharmacia Biotech; Piscataway, N.J.)

In yet another embodiment, the fusion protein is an immunoglobulin fusion protein in which all or part of a lysosomal protein of the invention is fused to sequences derived from a member of the immunoglobulin protein family, including immunoglobulins that serve as targeting moieties.

Chimeric and fusion proteins of the invention can be produced by standard recombinant DNA techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, e.g., Ausubel et al., supra). Moreover, many expression vectors are commercially available that already encode a fusion moiety (e.g., a GST protein). A nucleic acid encoding a lysosomal protein of the invention can be cloned into such an expression vector such that the fusion moiety is linked in-frame to the lysosomal protein of the invention.

The proteins of the invention can exhibit post-translational modifications, including, but not limited to glycosylations, (e.g., N-linked or O-linked glycosylations), myristylations, palmitylations, acetylations and phosphorylations (e.g., serine/threonine or tyrosine). In one embodiment, the lysosomal proteins of the invention exhibit reduced levels of O-linked glycosylation and/or N-linked glycosylation relative to endogenously expressed lysosomal proteins. In another embodiment, the lysosomal proteins of the invention do not exhibit O-linked glycosylation or N-linked glycosylation.

5.2 Nucleic Acids of the Invention

One aspect of the invention pertains to isolated nucleic acid molecules that encode a lysosomal protein of the invention, as well as nucleic acid molecules sufficient for use as hybridization probes to identify nucleic acid molecules encoding a lysosomal protein of the invention and fragments of such nucleic acid molecules suitable for use as PCR primers for the amplification or mutation of nucleic acid molecules. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

An "isolated" nucleic acid molecule is one which is separated from other nucleic acid molecules which are present in the natural source of the nucleic acid molecule. Preferably, an "isolated" nucleic acid molecule is free of sequences (preferably protein encoding sequences) which naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kB, 4 kB, 3 kB, 2 kB, 1 kB, 0.5 kB or 0.1 kB of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized. As used herein, the term "isolated" when referring to a nucleic acid molecule does not include an isolated chromosome.

In instances wherein the nucleic acid molecule is a cDNA or RNA, e.g., mRNA, molecule, such molecules can include a poly A "tail", or, alternatively, can lack such a 3' tail. Although cDNA or RNA nucleotide sequences may be depicted herein with such tail sequences, it is to be understood that cDNA nucleic acid molecules of the invention are also intended to include such sequences lacking the depicted poly A tails.

A nucleic acid molecule of the present invention can be isolated using standard molecular biology techniques. Sequence information for mammalian lysosomal proteins and encoding nucleic acids, including allelic variants, is commonly known in the art. Using all or a portion of the nucleic acid sequences as a hybridization probe, nucleic acid molecules of the invention can be isolated using standard hybridization and cloning techniques (e.g., as described in Sambrook et al., eds., *Molecular Cloning: A Laboratory Manual*, 2nd ed., *Cold Spring Harbor Laboratory*, Cold Spring Harbor Laboratory Press, Cold Spring Harbor, N.Y., 1989).

A nucleic acid molecule of the invention can be amplified using cDNA, mRNA or genomic DNA as a template and appropriate oligonucleotide primers according to standard PCR amplification techniques. The nucleic acid so amplified can be cloned into an appropriate vector and characterized by DNA sequence analysis. Furthermore, oligonucleotides corresponding to all or a portion of a nucleic acid molecule of the invention can be prepared by standard synthetic techniques, e.g., using an automated DNA synthesizer.

A nucleic acid fragment encoding a biologically active portion of a lysosomal protein of the invention can be prepared by isolating a portion a nucleic acid encoding a lysosomal protein and expressing the encoded portion of the protein (e.g., by recombinant expression in vitro) and assessing the activity of the encoded portion. Methods of assessing the activity of lysosomal proteins are well known in the art.

In addition to naturally-occurring allelic variants of a nucleic acid molecule of the invention sequence that may exist in the population, the skilled artisan will further appreciate that changes can be introduced by mutation thereby leading to changes in the amino acid sequence of the encoded protein, without altering the biological activity of the protein. For example, one can make nucleotide substitutions leading to amino acid substitutions at "non-essential" amino acid residues. A "non-essential" amino acid residue is a residue that can be altered from the naturally-occurring sequence without altering the biological activity, whereas an "essential" amino acid residue is required for biological activity. For example, amino acid residues that are not conserved or only semi-conserved among homologues of various species may be non-essential for activity and thus would be likely targets for alteration. Alternatively, amino acid residues that are conserved among the homologues of various species (e.g., mouse and human) may be essential for activity and thus would not be likely targets for alteration.

Accordingly, another aspect of the invention pertains to nucleic acid molecules encoding a lysosomal protein of the invention that contain changes in amino acid residues that are not essential for activity relative to wild type proteins. Such proteins differ in amino acid sequence from the wild type proteins yet retain biological activity. In one embodiment, the isolated nucleic acid molecule includes a nucleotide sequence encoding a protein that includes an amino acid sequence that is at least about 95% or 98% identical to the amino acid sequence of a lysosomal protein.

An isolated nucleic acid molecule encoding a variant protein can be created by introducing one or more nucleotide substitutions, additions or deletions into the nucleotide sequence of the open reading frame of the lysosomal protein such that one or more amino acid substitutions, additions or deletions are introduced into the encoded protein. Mutations can be introduced by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity. Following mutagenesis, the encoded protein can be expressed recombinantly and the activity of the protein can be determined.

5.3 Targeting Moieties

The targeting moieties suitable for delivering lysosomal proteins according to the methods of the invention are those that recognize cell surface molecules on target cells of interest and that facilitate non-clathrin mediated uptake of the lysosomal proteins particles into the target cells of interest upon binding by the protein or particle containing the targeting moiety.

In a preferred embodiment, the cell surface molecule bound by a targeting moeity is Intercellular Adhesion Molecule (ICAM)-1. ICAM-1 an Ig-like transmembrane glycoprotein expressed at the luminal surface of endothelial cells and other cell types (e.g., epithelial, glial and Schwann cells, monocytes and macrophages, myocytes), functionally involved in leukocyte transmigration (Springer, 1994, Cell 76:301-314; Almenar-Queralt et al., 1995, Am. J. Pathol. 147:1278-1288; Diamond et al., 1991, Cell 65:961-971). ICAM-1 is particularly useful for lysosomal enzyme replacement therapy, because its level of expression is greatly enhanced by cytokines and other pathological factors pertinent to inflammation, which is a component of lysosomal storage disease, and its blocking by the binding of a targeting moiety likely provides secondary anti-inflammatory benefits.

Another cell surface molecular that is suitable as a target for lysosomal protein delivery is Platelet Endothelial Cell Adhesion Molecule-1 (PECAM-1/CD31), a tyrosine phosphoprotein highly expressed on endothelial cells and leukocytes (see, e.g., Newman, 1997, J. Clin. Invest. 99(1):3-8).

In certain embodiments, the target cell surface molecule is a caveolar-associated receptors or other plasma membrane components. Examples of such receptors or other plasma membrane components include, but are not limited to, GPI-anchored proteins (e.g., alkaline phosphatase, urokinase plasminogen activator receptor, RHAMM,); thrombomodilin; PV1; glycolipids (GM1 mono-, di-, and triasialogangliosides); HLA; high affinity folate receptor; insulin receptor; muscarinic cholinergic receptors; VEGF receptor; connexins; gp90; albumin receptor gp60.

In certain embodiments, the target cell surface molecule is a phagocytosis-related receptor. Examples of such receptors include, but are not limited to, receptors: C3R; FcgammaR; LOX-1.

In certain embodiments, the target cell surface molecule is a receptor signaling for macropinocytosis. Examples of such receptors or proteins include, but are not limited to EGFR.

In certain embodiments, the target cell surface molecule is a cellular transmembrane aminopeptidase.

In certain embodiments, the targeted cell surface molecule is preferably a cell adhesion molecule ("CAM").

The targeting moeities can be antibodies or other, non-immunoglobulin proteins or peptides or ligands of another nature that bind to cell surface molecules. Exemplary methods of making antibodies suitable for use as targeting moieties are described below. Non-immunoglobulin proteins or peptides include ligands or binding partners. Where the cell surface molecule is capable of homophilic interactions, the targeting moiety can be a soluble form of the target cell surface molecule itself.

5.3.1 Antibodies

Accordingly, another aspect of the invention pertains to targeting moieties that are antibodies directed against a cell surface molecule present on a cell type to which delivery of a lysosomal protein is desirable. The term "antibody" as used herein refers to immunoglobulin molecules and immunologically active portions of immunoglobulin molecules, i.e., molecules that contain an antigen binding site which specifically binds an antigen, such as a cell surface molecule. Examples of immunologically active portions of immunoglobulin molecules include F(ab) and F(ab')$_2$ fragments which can be generated by treating the antibody with an enzyme such as pepsin. The invention provides polyclonal and monoclonal antibodies. The term "monoclonal antibody" or "monoclonal antibody composition", as used herein, refers to a population of antibody molecules that contain only one species of an antigen binding site capable of immunoreacting with a particular epitope.

An immunogen typically is used to prepare antibodies by immunizing a suitable subject, (e.g., rabbit, goat, mouse or other mammal). An appropriate immunogenic preparation can contain, for example, recombinantly expressed or chemically synthesized protein. The preparation can further include an adjuvant, such as Freund's complete or incomplete adjuvant, or similar immunostimulatory agent.

Polyclonal antibodies useful as targeting moieties can be prepared as described above by immunizing a suitable subject with a cell surface molecule as an immunogen. The antibody titer in the immunized subject can be monitored over time by standard techniques, such as with an enzyme linked immunosorbent assay (ELISA) using immobilized protein. If desired, the antibody molecules can be isolated from the mammal (e.g., from the blood) and further purified by well-known techniques, such as protein A chromatography to obtain the IgG fraction. At an appropriate time after immunization, e.g., when the specific antibody titers are highest, antibody-producing cells can be obtained from the subject and used to prepare monoclonal antibodies by standard techniques, such as the hybridoma technique originally described by Kohler and Milstein (1975) *Nature* 256:495-497, the human B cell hybridoma technique (Kozbor et al. (1983) *Immunol. Today* 4:72), the EBV-hybridoma technique (Cole et al. (1985), *Monoclonal Antibodies and Cancer Therapy*, Alan R. Liss, Inc., pp. 77-96) or trioma techniques. The technology for producing hybridomas is well known (see generally *Current Protocols in Immunology* (1994) Coligan et al. (eds.) John Wiley & Sons, Inc., New York, N.Y.). Hybridoma cells producing a monoclonal antibody of the invention are detected by screening the hybridoma culture supernatants for antibodies that bind the cell surface molecule, e.g., using a standard ELISA assay.

Alternative to preparing monoclonal antibody-secreting hybridomas, a targeting moeity that is a monoclonal antibody directed against a cell surface molecule can be identified and isolated by screening a recombinant combinatorial immunoglobulin library (e.g., an antibody phage display library) with the cell surface molecule. Kits for generating and screening phage display libraries are commercially available (e.g., the Pharmacia *Recombinant Phage Antibody System*, Catalog No. 27-9400-01; and the Stratagene *SurfZAP™ Phage Display Kit*, Catalog No. 240612). Additionally, examples of methods and reagents particularly amenable for use in generating and screening antibody display library can be found in, for example, U.S. Pat. No. 5,223,409; PCT Publication No. WO 92/18619; PCT Publication No. WO 91/17271; PCT Publication No. WO 92/20791; PCT Publication No. WO 92/15679; PCT Publication No. WO 93/01288; PCT Publication No. WO 92/01047; PCT Publication No. WO 92/09690; PCT Publication No. WO 90/02809; Fuchs et al. (1991) *Bio/Technology* 9:1370-1372; Hay et al. (1992) *Hum. Antibod. Hybridomas* 3:81-85; Huse et al. (1989) *Science* 246:1275-1281; Griffiths et al. (1993) *EMBO J.* 12:725-734.

Additionally, recombinant antibodies, such as chimeric and humanized monoclonal antibodies, comprising both human and non-human portions, which can be made using standard recombinant DNA techniques, are within the scope of the invention. A chimeric antibody is a molecule in which different portions are derived from different animal species, such as those having a variable region derived from a murine mAb and a human immunoglobulin constant region. (See, e.g., Cabilly et al., U.S. Pat. No. 4,816,567; and Boss et al., U.S. Pat. No. 4,816,397, which are incorporated herein by reference in their entirety.) Humanized antibodies are antibody molecules from non-human species having one or more complementarily determining regions (CDRs) from the non-human species and a framework region from a human immunoglobulin molecule. (See, e.g., Queen, U.S. Pat. No. 5,585,089, which is incorporated herein by reference in its entirety.) Such chimeric and humanized monoclonal antibodies can be produced by recombinant DNA techniques known in the art, for example using methods described in PCT Publication No. WO 87/02671; European Patent Application 184,187; European Patent Application 171,496; European Patent Application 173,494; PCT Publication No. WO 86/01533; U.S. Pat. No. 4,816,567; European Patent Application 125,023; Better et al. (1988) *Science* 240:1041-1043; Liu et al. (1987) *Proc. Natl. Acad. Sci. USA* 84:3439-3443; Liu et al. (1987) *J. Immunol.* 139:3521-3526; Sun et al. (1987) *Proc. Natl. Acad. Sci. USA* 84:214-218; Nishimura et al. (1987) *Canc. Res.* 47:999-1005; Wood et al. (1985) *Nature* 314:446-449; and Shaw et al. (1988) *J. Natl. Cancer Inst.* 80:1553-1559); Morrison (1985) *Science* 229:1202-1207; Oi et al. (1986) *Bio/Techniques* 4:214; U.S. Pat. No. 5,225,539; Jones et al. (1986) *Nature* 321:552-525; Verhoeyan et al. (1988) *Science* 239:1534; and Beidler et al. (1988) *J. Immunol.* 141:4053-4060.

Completely human antibodies are particularly desirable for therapeutic treatment of human patients. Such antibodies can be produced using transgenic mice which are incapable of expressing endogenous immunoglobulin heavy and light chains genes, but which can express human heavy and light chain genes. The transgenic mice are immunized in the normal fashion with a selected antigen, e.g., the extracellular portion of a cell surface molecule to which the targeted moiety is directed. Monoclonal antibodies directed against the antigen can be obtained using conventional hybridoma technology. The human immunoglobulin transgenes harbored by the transgenic mice rearrange during B cell differentiation, and subsequently undergo class switching and somatic mutation. Thus, using such a technique, it is possible to produce IgG, IgA and IgE antibodies. For an overview of this technology for producing human antibodies, see Lonberg and Huszar (1995, *Int. Rev. Immunol.* 13:65-93). For a detailed discussion of this technology for producing human antibodies and human monoclonal antibodies and protocols for producing such antibodies, see, e.g., U.S. Pat. Nos. 5,625,126; 5,633,425; 5,569,825; 5,661, 016; and No. 5,545,806. In addition, companies such as Abgenix, Inc. (Freemont, Calif.), can be engaged to provide human antibodies directed against a selected antigen using technology similar to that described above.

Completely human antibodies which recognize a selected epitope can be generated using a technique referred to as "guided selection." In this approach a selected non-human monoclonal antibody, e.g., a mouse antibody, is used to guide the selection of a completely human antibody recognizing the same epitope. (Jespers et al. (1994) *Bio/technology* 12:899-903).

5.4 Recombinant Expression Vectors and Host Cells

Another aspect of the invention pertains to vectors, preferably expression vectors, containing a nucleic acid encoding a lysosomal protein of the invention (or a portion thereof). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors, expression vectors, are capable of directing the expression of genes to which they are operably linked. In general, expression vectors of utility in recombinant DNA techniques are often in the form of plasmids (vectors). However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell. This means that the recombinant expression vectors include one or more regulatory sequences, selected on the basis of the host cells to be used for expression, which is operably linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel, *Gene Expression Technology: Methods in Enzymology* 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce lysosomal proteins, including fusion proteins.

The recombinant expression vectors of the invention can be designed for expression of a lysosomal protein of the invention in prokaryotic (e.g., *E. coli*) or eukaryotic cells (e.g., insect cells (using baculovirus expression vectors), yeast cells or mammalian cells). Suitable host cells are discussed further in Goeddel, supra. Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith and Johnson (1988) *Gene* 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Examples of suitable inducible non-fusion *E. coli* expression vectors include pTrc (Amann et al., (1988) *Gene* 69:301-315) and pET 11d (Studier et al., *Gene Expression Technology: Methods in Enzymology* 185, Academic Press, San Diego, Calif. (1990) 60-89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21(DE3) or HMS174 (DE3) from a resident λ, prophage harboring a T7 gn1 gene under the transcriptional control of the lacUV 5 promoter.

One strategy to maximize recombinant protein expression in *E. coli* is to express the protein in a host bacteria with an impaired capacity to proteolytically cleave the recombinant protein (Gottesman, *Gene Expression Technology: Methods in Enzymology* 185, Academic Press, San Diego, Calif. (1990) 119-128). Another strategy is to alter the nucleic acid sequence of the nucleic acid to be inserted into an expression vector so that the individual codons for each amino acid are those preferentially utilized in *E. coli* (Wada et al. (1992) *Nucleic Acids Res.* 20:2111-2118). Such alteration of nucleic acid sequences of the invention can be carried out by standard DNA synthesis techniques.

In another embodiment, the expression vector is a yeast expression vector. Examples of vectors for expression in yeast *S. cerivisae* include pYepSec1 (Baldari et al. (1987) *EMBO J.* 6:229-234), pMFa (Kurjan and Herskowitz, (1982) *Cell* 30:933-943), pJRY88 (Schultz et al. (1987) *Gene* 54:113-123), pYES2 (Invitrogen Corporation, San Diego, Calif.), and pPicZ (Invitrogen Corp, San Diego, Calif.).

Alternatively, the expression vector is a baculovirus expression vector. Baculovirus vectors available for expression of proteins in cultured insect cells (e.g., Sf 9 cells) include the pAc series (Smith et al. (1983) *Mol. Cell Biol.* 3:2156-2165) and the pVL series (Lucklow and Summers (1989) *Virology* 170:31-39).

In yet another embodiment, a nucleic acid of the invention is expressed in mammalian cells using a mammalian expression vector. Examples of mammalian expression vectors include pCDM8 (Seed (1987) *Nature* 329:840) and pMT2PC (Kaufman et al. (1987) *EMBO J.* 6:187-195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook et al., supra.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) *Genes Dev.* 1:268-277), lymphoid-specific promoters (Calame and Eaton (1988) *Adv. Immunol.* 43:235-275), in particular promoters of T cell receptors (Winoto and Baltimore (1989) *EMBO J.* 8:729-733) and immunoglobulins (Banerji et al. (1983) *Cell* 33:729-740; Queen and Baltimore (1983) *Cell* 33:741-748), neuron-specific promoters (e.g., the neurofilament promoter; Byrne and Ruddle (1989) *Proc. Natl. Acad. Sci. USA* 86:5473-5477), pancreas-specific promoters (Edlund et al. (1985) *Science* 230:912-916), and mammary gland-specific promoters (e.g., milk whey promoter; U.S. Pat. No. 4,873,316 and European Application Publication No. 264,166).

Developmentally-regulated promoters are also encompassed, for example the mouse hox promoters (Kessel and Gruss (1990) *Science* 249:374-379) and the beta-fetoprotein promoter (Campes and Tilghman (1989) *Genes Dev.* 3:537-546).

Another aspect of the invention pertains to host cells into which a recombinant expression vector of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic (e.g., *E. coli*) or eukaryotic cell (e.g., insect cells, yeast or mammalian cells).

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid into a host cell, including calcium phosphate or calcium chloride co-precipitation, DEAE-dextran-mediated transfection, lipofection, or electroporation. Suitable methods for transforming or transfecting host cells can be found in Sambrook, et al. (supra), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., for resistance to antibiotics) is generally introduced into the host cells along with the gene of interest. Preferred selectable markers include those which confer resistance to drugs, such as G418, hygromycin and methotrexate. Cells stably transfected with the introduced nucleic acid can be identified by drug selection (e.g., cells that have incorporated the selectable marker gene will survive, while the other cells die).

A typical mammalian expression vector contains at least one promoter element, which mediates the initiation of transcription of mRNA, the lysosomal protein coding sequence, and signals required for the termination of transcription and polyadenylation of the transcript. Additional elements include enhancers, Kozak sequences and intervening sequences flanked by donor and acceptor sites for RNA splicing. Highly efficient transcription can be achieved with the early and late promoters from SV40, the long terminal repeats (LTRS) from Retroviruses, e.g., RSV, HTLVI, HIVI and the early promoter of the cytomegalovirus (CMV). However, cellular elements can also be used (e.g., the human actin promoter). Suitable expression vectors for use in practicing the present invention include, for example, vectors such as pIRES1neo, pRetro-Off, pRetro-On, PLXSN, or pLNCX (Clonetech Labs, Palo Alto, Calif.), pcDNA3.1 (+/−), pcDNA/Zeo (+/−) or pcDNA3.1/Hygro (+/−) (Invitrogen), PSVL and PMSG (Pharmacia, Uppsala, Sweden), pRSVcat (ATCC 37152), pSV2dhfr (ATCC 37146) and pBC12MI (ATCC 67109). Mammalian host cells that could be used include human Hela 293, H9 and Jurkat cells, mouse NIH3T3 and C127 cells, Cos 1, Cos 7 and CV 1, quail QC1-3 cells, mouse L cells and Chinese hamster ovary (CHO) cells.

Alternatively, the gene can be expressed in stable cell lines that contain the gene integrated into a chromosome. The co-transfection with a selectable marker such as dhfr, gpt, neomycin, or hygromycin allows the identification and isolation of the transfected cells.

The transfected gene can also be amplified to express large amounts of the lysosomal protein. The DHFR (dihydrofolate reductase) marker is useful to develop cell lines that carry several hundred or even several thousand copies of the gene of interest. Another useful selection marker is the enzyme glutamine synthase (GS) (Murphy, et al., Biochem. J. 227:277-279 (1991); Bebbington, et al., Bio/Technology 10:169-175 (1992)). Using these markers, the mammalian cells are grown in selective medium and the cells with the highest resistance are selected. These cell lines contain the amplified gene(s) integrated into a chromosome. Chinese hamster ovary (CHO) and NSO cells are often used for the production of antibodies.

The expression vectors pC1 and pC4 contain the strong promoter (LTR) of the Rous Sarcoma Virus (Cullen, et al., Molec. Cell. Biol. 5:438-447 (1985)) plus a fragment of the CMV-enhancer (Boshart, et al., Cell 41:521-530 (1985)). Multiple cloning sites, e.g., with the restriction enzyme cleavage sites BamHI, XbaI and Asp718, facilitate the cloning of the gene encoding the lysosomal protein. The vectors contain in addition the 3' intron, the polyadenylation and termination signal of the rat preproinsulin gene.

In another embodiment, the expression characteristics of an endogenous lysosomal protein within a cell or cell line may be modified by inserting a DNA regulatory element heterologous to the endogenous gene of interest into the genome of a cell or stable cell line such that the inserted regulatory element is operatively linked with the endogenous gene encoding the lysosomal protein and controls, modulates or activates. For example, genes that are normally "transcriptionally silent," genes that is normally not expressed, or are expressed only at very low levels in a cell line, may be activated by inserting a regulatory element which is capable of promoting the expression of a normally expressed gene product in that cell line or microorganism. Alternatively, transcriptionally silent, endogenous genes may be activated by insertion of a promiscuous regulatory element that works across cell types.

A heterologous regulatory element may be inserted into a stable cell line such that it is operatively linked with and activates expression of endogenous genes encoding lysosomal proteins, using techniques, such as targeted homologous recombination, which are well known to those of skill in the art, and described, e.g., in Chappel, U.S. Pat. No. 5,272,071; PCT publication No. WO 91/06667, published May 16, 1991.

A host cell of the invention, such as a prokaryotic or eukaryotic host cell in culture, can be used to produce a lysosomal protein of the invention. Accordingly, the invention further provides methods for producing a lysosomal protein of the invention using the host cells of the invention. In one embodiment, the method comprises culturing the host cell of invention (into which a recombinant expression vector encoding a lysosomal protein of the invention has been introduced) in a suitable medium such that the protein is produced. In another embodiment, the method further comprises isolating the protein from the medium or the host cell.

5.5 Particles Comprising Lysosomal Proteins

The lysosomal proteins of the invention can be formulated into particles useful for therapeutic administration.

Particles of the invention can also be made by cross-linking lysosomal proteins and targeting moieties, either as separate molecules or as fusion proteins. The proteins are preferably cross-linked after their purification. In one embodiment, chemical crosslinking is used. Chemical crosslinking methods, e.g., glutaraldehyde crosslinking, may be used, for example by incubating 1-2 mg of lysosomal protein in the presence of 0.002% glutaraldehyde for 2 hours. Glutaraldehyde is removed by dialysis against phosphate buffered saline (PBS) overnight (Lussow et al., 1991, Eur. J. Immunol. 21: 2297-2302). In another embodiment, the lysosomal proteins are crosslinked by ultraviolet (UV) crosslinking. Alternatively, the targeting moiety and the lysosomal protein can be cross-linked using the avidin/streptavidin-biotin system, as described in the Examples below.

The lysosomal proteins and targeting moieties, can be absorbed directly onto the surface of a particle, either as separate molecules or as fusion proteins. The Examples below demonstrate direct adsorption of anti-ICAM antibody and the lysosomal protein acid sphingomyelinase to the surface of FITC latex beads.

The particles containing the lysosomal proteins of the invention can be microparticles. Examples of microparticles include liposomes, polymeric nanoparticles, microcapsules, or microspheres.

Any method of preparing particles for therapeutic administration can be used to generate particles comprising lysosomal proteins and targeting moieties (either as separate entities or as fusion proteins).

A number of suitable devices are known, including microparticles made of synthetic polymers such as polyhydroxy acids such as polylactic acid, polyglycolic acid and copolymers thereof, polyorthoesters, polyanhydrides, and polyphosphazenes, and natural polymers such as collagen, polyamino acids, albumin and other proteins, alginate and other polysaccharides, and combinations thereof (see, e.g., U.S. Pat. No. 5,814,599). Specific examples of particulate carriers include those derived from polymethyl methacrylate polymers, as well as microparticles derived from poly(lactides) (see, e.g., U.S. Pat. No. 3,773,919), poly(lactide-co-glycolides), known as PLG (see, e.g., U.S. Pat. No. 4,767,628) and polyethylene glycol, known as PEG (see, e.g., U.S. Pat. No. 5,648,095). Polymethyl methacrylate polymers are nondegradable while PLG particles biodegrade by random nonenzymatic hydrolysis of ester bonds to lactic and glycolic acids, which are excreted along normal metabolic pathways.

U.S. Pat. No. 5,648,095 describes the use of microspheres with encapsulated pharmaceuticals as drug delivery systems for nasal, oral, pulmonary and oral delivery. Slow-release formulations containing various polypeptides have also been described. See, e.g., International Publication No. WO 94/12158, U.S. Pat. No. 5,134,122 and International Publication No. WO 96/37216.

Other methods of forming microparticles are known. U.S. Pat. No. 6,884,435, for example, describes a method of forming microparticles which comprises combining a polymer with an organic solvent, then adding an emulsion stabilizer, such as the surfactant polyvinyl alcohol (PVA), then evaporating the organic solvent, thereby forming microparticles. The surface of the microparticles comprises the polymer and the stabilizer.

WO 00/06123 discloses methods of making microparticles having adsorbed macromolecules, such as proteins. The microparticles comprise, for example, a polymer such as a poly(alpha-hydroxy acid) (e.g., PLG), a polyhydroxy butyric acid, a polycaprolactone, a polyorthoester, a polyanhydride, and the like, and are formed using, for example, cationic, anionic or nonionic detergents.

In certain embodiments, the lysosomal proteins of the invention are formulated into liposomes. Liposomes include emulsions, foams, micelles, polimerosomes, filomicelles, insoluble monolayers, liquid crystals, phospholipid dispersions, lamellar layers and the like. In these preparations the lysosomal protein and targeting moeity are incorporated as part of a liposome, as separate molecules or as a fusion protein. Liposomes for use in the invention are formed from standard vesicle-forming lipids, which generally include neutral and negatively charged phospholipids and a sterol, such as cholesterol. The selection of lipids is generally guided by consideration of, e.g., liposome size, acid lability and stability of the liposomes in the blood stream. A variety of methods are available for preparing liposomes, as described in, e.g., Szoka et al., 1980, Ann. Rev. Biophys. Bioeng. 9:467, and U.S. Pat. Nos. 4,235,871; 4,501,728; 4,837,028; and 5,019,369.

Although previous studies indicated that the optimal conjugate size for internalization via CAM-mediated endocytosis is 100-300 nm in diameter (Wiewrodt et al., 2002, Blood 99:912-922; Murciano et al., 2003 Blood 101:3977-3984), a more recent and detailed study (data not shown) has revealed that anti-ICAM conjugates of larger sizes are also efficiently internalized by cells (89±1.7%, 81.2±5.7%, and 94.4±5.6% internalization at 1 h incubation and 37° C. in the case of <300 nm, 1 µm, and 10 µm conjugates, respectively).

Thus, the particles useful for LSD therapy can vary broadly in size, and methods of controlling particle size are routine to those of skill in the art. In certain embodiments, the particles range from 20 nm to 50 µm. In specific embodiments, the particles range from 50 nm to 10 µm; from 100 nm to 5 µm; from 50 nm to 1 µm; from 50 nm to 1 µm; from 100 nm to 500 nm, or any other range from at least 20 nm, 50 nm, 75 nm, 100 nm, 150 nm, 200 nm, 250 nm, 300 nm, 400 nm or 500 nm at its lower limit to up to 200 nm, 300 nm, 500 nm, 750 nm, 1 µm, 2 µm, 3 µm, 5 µm, 10 µm, 20 µm, 30 µm or 50 µm at its upper limit.

In the examples presented herein, in which anti-ICAM/ASM conjugates were prepared by streptavidin cross-linking of biotinylated anti-ICAM and ASM (FIG. 1A right), the size of the conjugates can be controlled by a number of parameters, including the level of protein biotinylation, the ratio of biotinylated protein to streptavidin, incubation time and temperature (Shuvaev et al., 2004, Methods Mol Biol. 283:3-19). Particle size can be monitored by dynamic light scattering. Where particles are prepared by coupling both the lysosomal protein and the targeting moiety to a to polymeric carrier (as for ASM/anti-ICAM1 in FIG. 1A left), the initial size of the carrier will determine the size of the final conjugate (for example, 100 nm carriers render 200-250 nm conjugates).

5.6 Pharmaceutical Compositions

The lysosomal proteins and particles of the invention (also referred to herein as "active compounds") can be incorporated into pharmaceutical compositions suitable for administration. Such compositions typically comprise the nucleic acid molecule, protein, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersions. For intravenous administration, suitable carriers include physiological saline, bacteriostatic water, Cremophor EL™ (BASF; Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a lysosomal protein or particle of the invention) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed.

Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from a pressurized container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

As defined herein, a therapeutically effective amount of protein (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight.

The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a protein can include a single treatment or, preferably, can include a series of treatments. In a preferred example, a subject is treated with antibody, protein, or protein in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of lysosomal protein used for treatment may increase or decrease over the course of a particular treatment. Changes in dosage may result and become apparent from the results of diagnostic assays as known in the art.

The pharmaceutical compositions can be included in a container, pack, or dispenser together with instructions for administration.

5.7 Therapeutic Methods

The present invention provides for both prophylactic and therapeutic methods of treating a subject at risk of (or susceptible to) or having a disorder associated with aberrant expression or activity of a lysosomal protein of the invention. For example, lysosomal storage disorders characterized by mutant lysosomal proteins include, but are not limited to, glycogen storage disease type II (GSD II or Pompe Disease), GM1 gangliosidosis, Tay-Sachs disease, GM2 gangliosidosis (AB variant), Sandhoff disease, Fabry disease, Gaucher disease, metachromatic leukodystrophy, Krabbe disease, Niemann-Pick disease (Types A-D), Farber disease, Wolman disease, Hurler Syndrome (MPS III), Scheie Syndrome (MPS IS), Hurler-Scheie Syndrome (MPS IH/S), Hunter Syndrome (MPS II), Sanfilippo A Syndrome (MPS IIIA), Sanfilippo B Syndrome (MPS IIIB), Sanfilippo C Syndrome (MPS IIIC), Sanfilippo D Syndrome (MPS IIID), Morquio A disease (MPS IVA), Morquio B disease (MPS IV B), Maroteaux-Lamy disease (MPS VI), Sly Syndrome (MPS VII), α-mannosidosis, β-mannosidosis, fucosidosis, aspartylglucosaminuria, sialidosis (mucolipidosis I), mucolipidosis II (I-Cell disease), mucolipidosis III (pseudo-Hurler polydystrophy), mucolipidosis IV, galactosialidosis (Goldberg Syndrorme), Schindler disease, cystinosis, Salla disease, infantile sialic acid storage disease, Batten disease (juvenile neuronal ceroid lipofuscinosis), infantile neuronal ceroid lipofuscinosis, and prosaposin. In certain embodiments, the lysosomal storage disorder displays a non-neurological pathology (e.g., Fabry, NPD-B, Gaucher).

For use to treat or prevent a disease condition, e.g., a lysosomal storage disease, the lysosomal proteins or particles of the invention, or pharmaceutical compositions thereof, are administered or applied in a therapeutically effective amount. A therapeutically effective amount is an amount effective to ameliorate or prevent the symptoms, or prolong the survival of, the patient being treated. Determination of a therapeutically effective amount is well within the capabilities of those skilled in the art.

The subject to be treated in accordance with the methods of the invention can be any mammal, e.g., cat, dog, cow, monkey, rabbit, but is most preferably a human subject.

5.8 Kits

The compositions of the invention—including lysosomal proteins, targeting moieties, nucleic acids and particles—may, if desired, be presented in a pack or dispenser device. For therapeutic products, the pack or dispenser which may contain one or more unit dosage forms containing the active ingredient. The pack may for example comprise metal or plastic foil, such as a blister pack. The pack or dispenser device may be accompanied by instructions for administration.

The invention also provides kits for carrying out the therapeutic regimens of the invention. Such kits comprise in one or more containers therapeutically or prophylactically effective amounts of the lysosomal proteins or particles, preferably purified, in pharmaceutically acceptable form. The lysosomal proteins or particles in a vial of a kit of the invention may be in the form of a pharmaceutically acceptable solution, e.g., in combination with sterile saline, dextrose solution, or buffered solution, or other pharmaceutically acceptable sterile fluid. Alternatively, the lysosomal proteins or particles may be lyophilized or desiccated; in this instance, the kit optionally further comprises in a container a pharmaceutically acceptable solution (e.g., saline, dextrose solution, etc.), preferably sterile, to reconstitute the lysosomal proteins or particles to form a solution for injection purposes.

The invention also provides kits for making the lysosomal proteins or particles of the invention. For example, in certain embodiments, the kits may contain one or more of the following components: a nucleic acid encoding a lysosomal protein of the invention (including a lysosomal protein that is fused to a targeting moiety); a nucleic acid encoding a targeting moiety; a cell line for expressing the above nucleic acid(s); a lysosomal protein of the invention (including a lysosomal protein that is fused to a targeting moiety); a targeting moiety; a cross-linking or conjugation reagent; and/or any of the components described in Section 5.5 that are useful for generating a particle of the invention, such as a liposome or a synthetic carrier particle. Optionally, the kit may further comprise instructions for its use to generate the lysosomal protein or particle of the invention.

In another embodiment, a kit of the invention further comprises a needle or syringe, preferably packaged in sterile form, for injecting the lysosomal proteins or particles, and/or a packaged alcohol pad. Instructions are optionally included for administration of the lysosomal proteins or particles by a clinician or by the patient.

6. EXAMPLES

The data described herein demonstrate that targeting recombinant lysosomal proteins to non-related surface proteins (e.g., taking ASM and ICAM-1 as examples of a lysosomal protein enzymatic cargo and target molecule, respectively) provides an alternative means for the treatment of LSD by ERT. Non-modified recombinant ASM and ICAM-targeted ASM were compared in terms of total delivery and targeting specificity in animal models and also in terms of binding, internalization, lysosomal trafficking capacity and activity in situ in cell cultures.

6.1 Construction and Characterization of ASM/Anti-ICAM Antibody Conjugates

The ability of recombinant ASM to be coupled to anti-ICAM antibodies to obtain internalizable-size conjugates retaining ASM activity and ICAM-1 targeting capacity was tested. Anti-ICAM/ASM conjugates were prepared either by coating ASM and anti-ICAM-1 to the surface of 100 nm fluorescent latex beads or by crosslinking biotinylated ASM and anti-ICAM-1 with streptavidin molecules (FIG. 1A). The size of resulting conjugates was within the range permissive for CAM-mediated internalization (e.g., 100-250 nm in diameter; FIG. 1B), also the conjugates showed ASM activity at acidic pH when measured in vitro (FIG. 1C).

Anti-ICAM/ASM conjugates bind to cultured encothelial cells (FIG. 2B) similarly to control anti-ICAM conjugates (FIG. 2A). The specificity of targeting is confirmed by the fact that control IgG conjugates poorly bind to endothelial cells (not shown). Moreover, only anti-ICAM/$^{125}$I-ASM conjugates but not untargeted $^{125}$I-ASM, showed significant total uptake in mouse lungs (21.5±1.8% ID), spleen (4.9±0.9% ID) and liver (50.9±0.7% ID), the major organs affected in Niemann-Pick type B disease (FIG. 3A). Anti-ICAM/$^{125}$I-ASM also accumulated in brain 1.7 fold over untargeted $^{125}$I-ASM. Particularly, anti-ICAM/$^{125}$I-ASM conjugates showed high capacity to target lungs (152.7±7.8% ID/g), an organ elusive to untargeted ASM (2.8±0.7% ID/g) or control IgG/125I-ASM conjugates (5.0±0.7% ID/g) (FIG. 3B). Also a study in endothelial cells in culture (e.g., human umbilical vein endothelial cells, HUVEC) confirmed the ability of anti-ICAM/ASM conjugates, but not untargeted ASM (165.5±20.6 vs 1.8±0.9 particles/cell), to bind to EC (FIG. 3C). Binding was inhibited by blocking ICAM-1, but not M6PR (3.3±0.8 vs 122.4±15.1% respect to control values), corroborating the specificity of targeting (FIG. 3D).

Secondly, the capacity and mechanism of internalization of anti-ICAM/ASM conjugates in control or ASM-deficient cells in culture as well as its efficiency was determined. Anti-ICAM/ASM was efficiently internalized by HUVEC at 37° C. after 2 h incubation (76.3±1%), but not 4° C. (17.6±5%), indicating internalization by an endocytic mechanism (FIG. 4A). The mechanism of conjugate internalization was sensitive to amiloride, an inhibitor of CAM-mediated endocytosis (67.6±4% of the control value), but not Monodansyl-cadaverine, an inhibitor of clathrin-mediated uptake (114.7±8% of the control value), which indicates that intracellular delivery of ASM is driven by anti-ICAM targeting moiety (FIG. 4B). Intracellular delivery of anti-ICAM/ASM conjugates was fast in both control EC ($t½ \approx 20$ min) and ASM-deficient skin fibroblast from NPD-B patients ($t½ \approx 25$); (FIG. 4C). Also, internalization of anti-ICAM/ASM conjugates in HUVEC treated with imipramine, e.g., an agent that degrades endogenous ASM and thus provides an ASM-deficient endothelial cell model, was efficient (95.9±2.5% of that in control HUVEC); (FIG. 4D). Intracellular delivery of anti-ICAM/ASM to endothelial cells was quantified. The data show that, within 1 h, endothelial cells internalized of anti-ICAM/ASM conjugates that bound to the cell surface (≈100 conjugate particles/cell) (FIG. 5). Thus, intracellular delivery of anti-ICAM/ASM to endothelial cells is efficient.

Thirdly, the stability and ability ASM delivered intracellularly by anti-ICAM conjugates to traffic to lysosomes was tested. Whereas anti-ICAM-1 targeting moiety was significantly degraded by 2-3 h after internalization within HUVEC (FIG. 6A), $^{125}$I-ASM remained stable at least for 5 h (last time determined) (FIG. 6B), also was converted to a lower molecular weight form (FIG. 6Ba), indicating a proper intracellular processing of this lysosomal enzyme. Moreover, anti-ICAM/ASM conjugates were efficiently delivered to lysosomes within 2-3 h after internalization within control HUVEC, imipramine-treated HUVEC and NPD-B fibroblasts (FIG. 6C).

Next, the activity of ICAM/ASM conjugates delivered intracellularly to ASM-deficient cells (e.g., imipramine HUVEC or NPD-B fibroblasts) was determined by testing their ability to revert intracellular accumulation of sphingomyelin. For this purpose, cells were first loaded with BODIPY-FLC12-sphingomyelin, which emits green fluorescence when degraded to ceramide or not aberrantly concentrated in intracellular organelles (FIG. 7A, control) or red fluorescence when undegraded and concentrated at lysosomes (FIG. 7A, IMP). Cells treated with anti-ICAM/ASM conjugates showed normal green-fluorescent staining in opposition to non-treated cells, indicating that ASM delivered by anti-ICAM conjugates is active within intracellular compartments (FIG. 7B).

Cholesterol level, which secondarily accumulates within cells as a result of sphigomyelin storage, was also decreased in intracellular vesicles containing anti-ICAM/ASM conjugates. In NPD-B fibroblast, unconjugated ASM only partially attenuated sphingomyelin accumulation, whereas anti-ICAM/ASM totally reverted the storage to background levels (Muro et al., unpublished results). Injection of anti-ICAM/ASM carrier in ASM knockout mice, a model for NPD, increased ASM activity over the endogenous levels in heart (1.5 fold), brain (1.5 fold), kidney (5.0 fold), liver (17.1 fold), lung (19.7 fold), and spleen (59.2 fold).

In addition, in contrast to anti-ICAM conjugates that traffic to lysosomes after internalization by cells, ICAM-1 recycled back to the plasma membrane (Muro et al., 2005, Blood 105(2):650-8). This allowed anti-ICAM conjugates to be efficiently targeted and internalized in a recurrent manner in cultured cells and in mice (Muro et al., 2005, Blood 105(2):650-8), providing the bases for sustained delivery and prolonged effects, which could be achieved with "stealth" biodegradable carriers. Biodegradable carriers targeted to ICAM-1 also efficiently bound to (95±18 carrier/cell) and internalized within HUVEC (83±3% internalization), and provided efficient ASM accumulation in mice organs (0.3±0.1, 1.4±0.1, 4.72±1.1, 23.9±2.4, and 43.7±6.6% ID in heart, kidney, spleen, lung, and liver, respectively).

Finally, a saturating dose of anti-ICAM conjugates internalized by endothelial cells in culture did not affect internalization (110±15% of control) or trafficking (89±11% of control) of dextran through classical endocytic pathways, cell viability (98±3% of control) (Muro et al., 2005, Blood 105(2):650-8), or endothelial permeability (transendothelial electrical resistance, $^{125}$I-albumin lung/blood ratio in mice).

NPD-B fibroblasts have been developed as a model to study anti-ICAM/ASM targeting. Skin fibroblasts from NPD-B patients manifest pathological alterations associated with genetic ASM-deficiency. FACS analysis showed that ICAM-1 expression in NPD-B skin fibroblasts is similar to that in control endothelial cells (FIG. 8), indicating that ICAM-1 targeting might be effective in NPD-B patients.

Therefore, targeting to a non-related surface protein, ICAM-1, provides efficient delivery of ASM to a variety of organs upon IV injection, and confers the enzyme high ability to enter cells and traffic to lysosomal compartments, where is active to revert aberrant accumulation of its substrate, sphingomyelin. Similar methods using ICAM-1 or other surface proteins may be applied to enzyme replacement therapy for LSD, improving the outcome for these conditions by providing a means to decrease the amount of the administered enzyme while increasing its effective uptake.

6.2 Therapeutic Efficacy of Anti-ICAM/ASM

The inventors expect that anti-ICAM/ASM injected in mice will be delivered to endo-lysosomal compartments within cells. To test this, the sub-cellular distribution of ASM in lungs by electron microscopy at given time intervals post intravenous injection of anti-ICAM/ASM in mice (tentatively 30, 60, and 180 min post-injection). The collected organs will be prepared for ultrastructure determination. The two conjugate moieties (rat anti-mouse ICAM and recombinant human ASM) will be detected using goat anti-rat IgG conjugated to 5 nm colloidal gold and rabbit anti-human ASM followed by goat anti-rabbit IgG attached to 15 nm gold particles. This will permit to identify whether conjugates deliver ASM within electron dense lysosomes. If in these animal experiments, EM may reveal cross-reactivity of anti-human ASM antibodies with endogenous murine ASM, we will detect anti-ICAM/ASM SA-crosslinked conjugates with biotin-conjugated gold particles or, alternatively, direct EM visualization of conjugates can be achieved by surface coating electron dense SA-latex particles with biotinylated anti-ICAM and ASM. In addition, ASM knockout mice will be utilized to avoid interference with the endogenous enzyme. Finally, Lamp-1 immunolabeling can be utilized to confirm lysosomal localization of anti-ICAM/ASM conjugates in animals by EM.

To study the effects of anti-ICAM/ASM in ASM knockout mice, three sets of mice are injected, each of them with a different conjugate dose: 2.5, 5, or 15 mg ASM/kg body weight and ASM activity post-injection determined. The level of ASM activity will be determined from tissue homogenates using BODIPY-FL$_{C12}$-sphingomyelin. The reaction products will be separated by thin layer chromatography (TLC), the bands containing the fluorescent ceramide will be scraped, extracted, and quantified by spectrofluorometry. ASM activity in non-treated ASMKO mice and wild-type C57BL/6 mice will be used as controls.

To test attenuation of NPD-B phenotype, ASMKO mice are injected with anti-ICAM/ASM conjugates every other day for 1 week (3 injections) and sacrificed 48 h after the last injection. Histological examination of lungs and other organs with Sudan Black will determine lipid accumulation. Lipids in the bronchioalveolar lavage fluid (BALF), lungs, and other tissue homogenates will be extracted and the levels of sphingomyelin will be determined from the phosphate content using an established protocol (Rousseau et al., 1986, Arch. Biochem. Biophys. 244:838-845).

Lung injury is examined by assessing pulmonary infiltration, edema, and tissue oxidation. Transmigration of white blood cells to the airways will be estimated from BALF. Hematoxylin-eosin staining will determine tissue morphology and cellular infiltration into the lung tissue. Accumulation of polymorphonuclear neutrophils in the pulmonary vasculature by myeloperoxydase activity in lung tissue is quantified as previously described (Christofidou-Solomidou et al., 2002, Am. J. Pathol. 160:1155-1169). Vascular permeability will be estimated from pulmonary edema, monitored by the wet-to dry ratio and protein level in the BALF. Lipid and protein oxidation will be determined by immunostaining using antibodies to the isoprostane iPF$_{2\alpha}$-III, which reflects lipid peroxidation, and nitrotyrosine, a product of oxidative protein nitration (Pratico et al., 1997, J. Clin. Invest. 100:2028-2034; Gole et al., 2000, Am. J. Physiol. Lung Cell Mol. Physiol. 278:L961-967).

In all cases, untreated C57BL/6 mice and ASM knockout mice will be used as controls to estimate the therapeutic effect of anti-ICAM/ASM conjugates on the pathological NPD-B phenotype. It is expected that doses ranging from 2 to 15 mg (ASM)/kg of body weight are sufficient to observe a reduction of the pulmonary pathology.

6.3 In Vivo Distribution and Therapeutic Efficacy of ASM/Anti-ICAM Antibody Conjugates 6.3.1 Analysis of ASM/Anti-ICAM Conjugates in Normal Animals To assess whether anti-ICAM/ASM conjugates injected into mice accumulates within endo-lysosomal compartments of the pulmonary EC, the sub-cellular distribution of ASM in lungs by electron microscopy is analyzed at given time intervals post intravenous injection of anti-ICAM/ASM in mice (tentatively 30, 60, and 180 min post-injection). The collected organs are prepared for ultrastructure determination. The two conjugate components (rat anti-mouse ICAM and recombinant human ASM) are detected using goat anti-rat IgG conjugated to 5 nm colloidal gold and rabbit anti-human ASM followed by goat anti-rabbit IgG attached to 15 nm gold particles. This allows the determination of whether conjugates deliver ASM within electron dense lysosomes.

If in these animal experiments EM reveals cross-reactivity of anti-human ASM antibodies with endogenous murine ASM, anti-ICAM/ASM SA-crosslinked conjugates can be detected with biotin-conjugated gold particles or, alternatively, direct EM visualization of conjugates can be achieved by surface coating electron dense SA-latex particles with biotinylated anti-ICAM and ASM. Alternatively, ASM knockout mice can be utilized to avoid interference with the endogenous enzyme. Finally, Lamp-1 immunolabeling can be utilized to confirm lysosomal localization of anti-ICAM/ASM conjugates in animals by EM.

6.3.2 Analysis of ASM/Anti-ICAM Conjugates in ASM Mutant Animals

The ASM deficient mouse model of Types A and B Niemann-Pick disease is used to demonstrate the clinical and pathological effectiveness of ERT using ICAM-1 directed ASM nanoparticles. Assessment techniques are essentially the same as those reported previously for ERT studies using free enzyme (Miranda et al., 2000, FASEB J. 14:1988-1995).

Three sets of mice are injected with ASM/anti-ICAM conjugates, each of them with a different conjugate dose: 2.5, 5, or 15 mg ASM/kg body weight, to determine ASM activity post-injection. The level of ASM activity is determined from tissue homogenates using BODIPY-FL$_{C12}$-sphingomyelin. The reaction products will be separated by thin layer chromatography (TLC), the bands containing the fluorescent ceramide will be scraped, extracted, and quantified by spectrofluorometry. ASM activity in non-treated ASMKO mice and wild-type C57BL/6 mice is used as controls.

Histological analysis of fixed tissues obtained after enzyme injection are performed to assess the degree of foam cell involvement. Tissues are harvested, lipid extracts prepared and the amount of stored sphingomyelin and free cholesterol quantified. Tissues examined include, but are not be limited to, liver, spleen, lung, kidney, heart and brain, organs that are affected in human NPD patients. Results using ICAM-1 directed ASM nanoparticles are compared to those obtained using free enzyme. ERT is initiated in young animals (1 month or below) and continued weekly until 4 months to assess prevention of storage disease. Other studies are initiated in 4 month old animals and continued weekly until 6 months to assess reversal of disease. In the lung, alveolar lavage fluid is harvested and the number of inflammatory cells, amount of stored phospholipid, and function of the alveolar macrophages determined. For neurological assessment animals are monitored weekly on an accelerating rotarod apparatus to quantify cerebellar function.

To test attenuation of NPD-B phenotype, ASMKO mice are injected with anti-ICAM/ASM conjugates every other day for 1 week (3 injections) and sacrificed 48 h after the last injection. Histological examination of lungs and other organs with Sudan Black is used determine lipid accumulation. Lipids in the bronchoalveolar lavage fluid (BALF), lungs, and other tissue homogenates are extracted and the levels of sphingomyelin will be determined from the phosphate content using an established protocol (Rousseau et al., 1986, Arch. Biochem. Biophys. 244:838-845).

Lung injury is also examined by assessing pulmonary infiltration, edema, and tissue oxidation. Transmigration of white blood cells to the airways is estimated from BALF. Hematoxylin-eosin staining is used to determine tissue morphology and cellular infiltration into the lung tissue. Accumulation of polymorphonuclear neutrophils in the pulmonary vasculature by myeloperoxydase activity in lung tissue is determined as previously described (Christofidou-Solomidou et al., 2002, Am. J. Pathol. 160:1155-1169). Vascular permeability is estimated from pulmonary edema, monitored by the wet-to dry ratio and protein level in the BALF. Lipid and protein oxidation will be determined by immunostaining using antibodies to the isoprostane iPF$_{2\alpha}$-III, which reflects lipid peroxidation, and nitrotyrosine, a product of oxidative protein nitration (Pratico et al., 1997, J. Clin. Invest. 100: 2028-2034; Gole et al., 2000, Am. J. Physiol. Lung Cell Mol. Physiol. 278:L961-967).

Untreated C57BL/6 mice and ASM knockout mice are used as controls to estimate the therapeutic effect of anti-ICAM/ASM conjugates on the pathological NPD-B phenotype. It is expected that doses ranging from 2 to 15 mg (ASM)/kg of body weight will be sufficient to observe a reduction of the pulmonary pathology.

6.4 General Applicability of ASM Studies to Other Lysosomal Proteins

The studies described herein demonstrate that the data obtained for ASM, anti-ICAM conjugates and NPD is applicable to other lysosomal proteins, other target molecules, and other LSDs.

In fibroblasts from normal individuals internalization of the fluid phase marker, dextran, was inhibited by the clathrin inhibitor, monodansyl cadaverine, to 54.7±7.2% of the control value, whereas in fibroblasts from Fabry, Gaucher, type C Niemann-Pick (NPC) and NPD patients this inhibition was not significant (92.1±13.5%, 109.8±9.3%, 111.4±9.9, and 88.9±12.1% of control values). These data suggest that although clathrin-mediated pathways account for internalization of dextran in normal cells, this pathway is not relevant in the case of LSD cells.

In addition, internalization of a specific ligand endocytosed by clathrin-coated pits, transferrin, (a pathway utilized as a mean to deliver drugs through the brain blood barrier; Zhang and Pardridge, 2005, J. Pharmacol. Exp. Ther. 313 (3):1075-81), was deficient in fibroblasts from patients with LSD (27.4±4.3% in Fabry, 21.1±3.2% in Gaucher, 30.1±1.2 in NPC, and 32.3±1.6% in NPD), as compared to normal cells. In contrast, CAM-mediated endocytosis of anti-ICAM conjugates was not affected in LSD cells vs. normal fibroblasts (77.5±7.5% in Fabry, 95.7±2.7% in Gaucher, 109.9±1.1 in NPC, and 103.9±0.8% in NPD).

In addition, incubation at 37° C. for 2 h resulted in similar internalization of anti-ICAM conjugates by endothelial cells under 9 dyn/cm$^2$ flow (86±5% of static cells), which was inhibited by amiloride but not monodansyl-cadaverine (43±4% vs. 92±3% of the control value). This result indicates that also under flow, anti-ICAM conjugates bypass clathrin-mediated pathways and are internalized by CAM-mediated endocytosis. Therefore, bypassing clathrin-dependent pathways, deficient in LSD, can be an effective delivery route of lysosomal proteins.

REFERENCES CITED

All references cited herein are incorporated herein by reference in their entirety and for all purposes to the same extent as if each individual publication or patent or patent application was specifically and individually indicated to be incorporated by reference in its entirety for all purposes.

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

What is claimed is:

1. A nucleic acid comprising a nucleotide sequence encoding a fusion protein comprising a mammalian acid sphingomyelinase or active fragment thereof covalently attached to a targeting moiety, wherein the targeting moiety binds to an extracellular portion of Intracellular Adhesion Molecule-1 (ICAM-1) or Platelet Endothelial Cell Adhesion Molecule (PECAM-1).

2. The nucleic acid of claim 1 in which the nucleotide sequence is operably linked to a promoter.

3. An isolated host cell which comprises in its genome the nucleic acid of claim 1.

4. A method for producing a fusion protein comprising a mammalian acid sphingomyelinase or active fragment thereof which is covalently attached to a targeting moiety, wherein the targeting moiety binds to an extracellular portion of Intracellular Adhesion Molecule-1 (ICAM-1) or Platelet Endothelial Cell Adhesion Molecule (PECAM-1), said method comprising:

(a) culturing the isolated host cell of claim 3 under conditions in which the mammalian acid sphingomyelinase or active fragment covalently attached to the targeting moiety is expressed and (b) recovering the expressed mammalian acid sphingomyelinase or active fragment covalently attached to the targeting moiety.

5. The method of claim 4, in which the isolated host cell is a mammalian cell in culture.

* * * * *